US007917192B2

(12) United States Patent
Dos Santos Varela

(10) Patent No.: US 7,917,192 B2
(45) Date of Patent: Mar. 29, 2011

(54) TOMOGRAPHY BY EMISSION OF POSITRONS (PET) SYSTEM

(75) Inventor: João Manuel Coelho Dos Santos Varela, Estoril (PT)

(73) Assignees: FFCUL/BEB-Fundacao Da Faculdade De Ciencias Da Universidade De Lisboa, Instituto De Biofisica E Engenharia Biomedia, Lisbon (PT); Universidade De Coimbra/Faculdade De Medicina-Instituto Biomedico De Investigaceo Da Luz E Imagem, Coimbra (PT); Inesc Inovacao-Instituto De Novas Tecnologia (INOV), Lisbon (PT); Inegi-Instituto De Engenharla Mecanica E Gestao Industrial, Leca Do Balio (PT); Tagusparque-Sociedade De Promocao E Desenvolvimento Do Parque De Ciencias E Tecnologia Da Area De Lisboa, S.A., Oeiras (PT); Lip-Laboratorio de Instrumentacao e Fisica Experimental de Particulas, Lisbon (PT); Hgo Hospital Garcia De Horta, Servicios De Medicina Nuclear, Almada (PT)

( * ) Notice: Subject to any disclaimer, the term of this patent is extended or adjusted under 35 U.S.C. 154(b) by 922 days.

(21) Appl. No.: 11/664,121

(22) PCT Filed: Sep. 30, 2005

(86) PCT No.: PCT/PT2005/000016
§ 371 (c)(1),
(2), (4) Date: Jul. 18, 2007

(87) PCT Pub. No.: WO2006/049523
PCT Pub. Date: May 11, 2006

(65) Prior Publication Data
US 2008/0103391 A1 May 1, 2008

(30) Foreign Application Priority Data
Sep. 30, 2004 (PT) .......................................... 103200

(51) Int. Cl.
*A61B 6/00* (2006.01)

(52) U.S. Cl. ................ 600/431; 250/370.1; 250/370.11; 250/370.13; 250/370.12

(58) Field of Classification Search .................. 600/431; 250/361, 301, 370, 363
See application file for complete search history.

(56) References Cited

U.S. PATENT DOCUMENTS
4,920,271 A 4/1990 Arnone
(Continued)

FOREIGN PATENT DOCUMENTS
EP 0 933 652 A 8/1999
(Continued)

OTHER PUBLICATIONS

Lerch M L F et al: "Readout of LYSO using a new silicon photodetector for positron emission tomography" 2003 IEEE Nuclear Science Symposium Conference Record. / 2003 IEEE Nuclear Science Symposium and Medical Imaging Conference. Portland, OR, Oct. 19-25, 2003, IEEE Nuclear Science Symposium Conference Record, New York, NY : IEEE, US, vol. vol. 5 of 5, Oct. 19, 2003, pp. 1408-1412 vol. 2, XP010736468 ISBN: 0-7803-8257-9 p. 1408-p. 1409.

(Continued)

*Primary Examiner* — Tse Chen
*Assistant Examiner* — Joel F Brutus
(74) *Attorney, Agent, or Firm* — Sughrue Mion, PLLC

(57) ABSTRACT

Tomography by emission of positrons (pet) system dedicated to examinations of human body parts such as the breast, axilla, head, neck, liver, heart, lungs, prostate region and other body extremities which is composed of at least two detecting plates (detector heads) with dimensions that are optimized for the breast, axilla region, brain and prostrate region or other extremities; motorized mechanical means to allow the movement of the plates under manual or computer control, making it possible to collect data in several orientations as needed for tomographic image reconstruction; an electronics system composed by a front-end electronics system, located physically on the detector heads, and a trigger and data acquisition system located off-detector in an electronic crate; a data acquisition and control software; and an image reconstruction and analysis software that allows reconstructing, visualizing and analyzing the data produced during the examination.

18 Claims, 7 Drawing Sheets

U.S. PATENT DOCUMENTS

Figure 1:
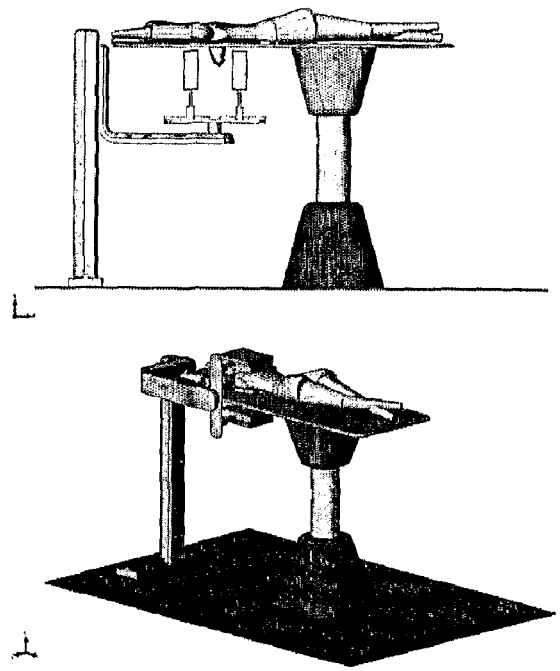

| | | |
|---|---|---|
| 5,757,006 A | 5/1998 | DeVito et al. |
| 6,624,420 B1 | 9/2003 | Chai et al. |
| 2002/0090050 A1 | 7/2002 | Nutt et al. |
| 2002/0163994 A1 | 11/2002 | Jones |
| 2003/0010925 A1 | 1/2003 | Watanabe |
| 2003/0105397 A1 | 6/2003 | Tumer et al. |
| 2003/0190065 A1 | 10/2003 | Hamill et al. |
| 2003/0210814 A1 | 11/2003 | Nelson |

FOREIGN PATENT DOCUMENTS

| | | | |
|---|---|---|---|
| WO | WO 98/27443 A | | 6/1998 |

OTHER PUBLICATIONS

Pepin C M et al: "Investigation of the properties of new scintillator LYSO and recent LSO scintillators for phoswich pet detectors" 2002 IEEE Nuclear Science Symposium Conference Record. / 2002 IEEE Nuclear Science Symposium and Medical Imaging Conference. Norfolk, VA, Nov. 10-16, 2002, IEEE Nuclear Science Symposium Conference Record, New York, NY : IEEE, US, vol. vol. 3 of 3, Nov. 10, 2002, pp. 655-660, XP010663616 ISBN: 0-7803-7636-6 p. 655.

Richard M Leahy et al: "Editorial Recent Developments in Iterative Image Reconstruction for PET and SPECT" IEEE Transactions on Medical Imaging, IEEE Service Center, Piscataway, NJ, US, vol. 19, No. 4, Jun. 2000, XP011035956 ISSN: 0278-0062 the whole document.

Kinahan P E et al: "Fast iterative image reconstruction of 3D PET data" Nuclear Science Symposium, 1996. Conference Record., 1996 IEEE Anaheim, CA, USA Nov. 2-9, 1996, New York, NY, USA, IEEE, US, vol. 3, Nov. 2, 1996, pp. 0-7803,3534-1 p. 1918.

Honeyman et al: "Nuclear medicine data communications" Seminars in Nuclear Medicine, Grune and Stratton, Orlando, FL, US, vol. 28, No. 2, Apr. 1998, pp. 158-164, XP005441069 ISSN: 0001-2998 abstract.

TOMOGRAPHY BY EMISSION OF POSITRONS (PET) SYSTEM

1. BACKGROUND OF THE INVENTION

For a long time, medical imaging was mainly based on the physical principles of X-Ray Radiography and ultrasonography. The progress on these two techniques occurred mainly at the level of image detection, software for image processing and data storing. Recently, other techniques, based on different physical mechanisms, gave to the field of medical imaging new horizons on the exploration of human body's morphology and functionality.

A recent example is Positron Emission Tomography, PET, mainly used on cancer detection, with proved effective cost-benefit in cancer detection, staging and evaluation of therapy efficacy. The underlying principle of PET systems, as any other nuclear medicine method, is the detection of gamma radiation from a radioactive substance injected into the human body. In PET, the radioactive substance includes radioisotopes of atoms existing in biological molecules and so, with more affinity to certain biochemical mechanisms and cells (e.g. glucose-based FDG is fixed preferentially by cancerous cells, due to their higher metabolic rate). The molecule used as a label of the physiopathological process is marked with a positron emission, which after annihilation with an atomic electron emits two mono-energetic photons in opposite directions. A radiation detection system is needed to identify the presence and the spatial origin of the photons. Spatial origin of the photons is determined by the intersection of several lines generated by the emission of photons pairs.

1.1 Cancer Detection

The early detection of cancer is becoming a priority in healthcare policy of an increasing number of countries. Particularly important is the detection of breast cancer. A very large number of women (about one woman in nine) will develop a breast cancer, which is the second leading cause of cancer death in women of all ages, and the leading cause of death in those aged 40 to 49. [L. W. Basset, Jackson V. P, Diagnosis of Diseases of the Breast. W. B. Saunders Company. 1997. Chapter 23]. On the other hand, early detection leads to very high cure rate [P. A. Newcomb, P. M. Lantz, Breast cancer research and treatment, 28(2), pp 97-106 (1993)].

Unfortunately the performance of conventional X-ray mammography is unsatisfactory. X-ray mammography has an overall sensitivity, number of true positive over total positive, of about 80%, depending on the breast type. For fatty breasts a sensitivity of 95% can be achieved with a lower limit in the size of a detectable tumor of about 5 mm, while for dense breasts the sensitivity drops to 70% with a lower limit in size of 10 to 20 mm. The size of the detectable tumor is important since the prognosis of cancer is related to its size. On the other hand, its specificity, the number of true negative over total negative, is rather low, typically around 30%. A large number of unnecessary biopsies or even axillary's dissections are therefore performed which have a high cost for the society, not considering the psychological aspect on the women.

On the other hand PET metabolic techniques using $^{18}$F-fluoro-deoxy-glucose (FDG) have demonstrated an excellent sensitivity to malignant tissues (nearly 100%) due to the much higher glucose consumption of cancerous cells as compared to normal tissue. PET using FDG as a tracer of tumor glucose metabolic activity is a non-invasive imaging technology which probes tissue and organs function rather than structure [U.S. Pat. No. 5,453,623, U.S. Pat. No. 5,961,457].

This invention responds to the demand for a highly specific PET device having a spatial resolution of the order of 1 mm in order to efficiently detect stage 1a cancers.

1.2 Motivations for a Functional Imaging Device

Morphologic methods, like conventional X-Ray mammography or echography, provide images of the variations of the tissues density inside the body. The correlation between denser regions and cancer tumors is not always easy to establish, moreover cancer is very often characterized by low contrast structures in the domain of low energy X-rays, which leads to low sensitivity. This is particularly true for the 40% of women having dense breasts, for which X-rays mammography misses about 50% of cancers.

The high rate of false positive leads to a large number of unnecessary biopsies: 60 to 85% of the biopsies following an imaging indication, obtained with X-rays or ultrasounds, do not correspond to malign pathology [L. P. Adler, Beast Imaging Conference, Rome, May 2000]. An estimation of 600,000 unnecessary biopsies per year in the US only, correspond to a cost of 1 B$. More dramatic is the too large number of false negative with often fatal consequences for the patient. Other approaches, like MRI (Magnetic Resonance Imaging) and echography have not proven yet to be more efficient than X-rays.

There is clearly a need for much higher sensitivity and specificity. Moreover breast cancer not only needs diagnosis, but the biological rating is becoming increasingly useful. Tumor cells are known to metabolize glucose much faster than normal cells. Positron emission tomography (PET) using $^{18}$F-fluoro-deoxy-glucose (FDG) as a radiotracer is therefore likely to have a high sensitivity. Indeed a meta analysis study performed on 259 patients [L. P. Adler, Beast Imaging Conference, Rome, May 2000] has given sensitivity (true positive/total positive) of 92%, specificity (true negative number/total negative number) of 94%, and accuracy (true positive number+negative/total number) of 92%.

Although the clinical series are still limited, Positron Emission Tomography appears to be able to bring a significant improvement in the breast cancer diagnosis. The following results have been obtained using $^{18}$F-FDG:

a. In the diagnosis of malign neoplasms, sensitivities that vary between 77% [Yutani K et al. Detectability of FDG-PET and MIBI-SPECT to breast tumor, J Nucl Med. 1997; 38: 68P] and 100% [Yutani K et al. Correlation of F-18-FDG and Tc-99m-MIBI uptake with proliferative activity in breast cancer [abstract]. J Nucl Med. 1999; 40: 16-17P] and specificities between 84% [Avril N et al. Metabolic characterization of breast tumours with positron emission tomography with F-18 fluorodeoxyglucose. J Clin Oncol. 1996; 14: 1848-1857] and 100% [Noh D et al. Diagnostic value of positron emission tomography for detecting breast cancer. World J. Surg. 1998; 22: 223-228] were observed;

b. In what concerns the diagnosis of ganglion loco-regional invasion, fundamental for the initial staging of the disease, values of sensibility and accuracy of the order of 97 and 93%, respectively, have been measured [Bender H. et al. Breast imaging with positron emission tomography. In: Taillefer R, Khalkhali I, Waxman AD et al. Eds. Radionuclide imaging of the breast. New York: Marcel Dekker, 1998: 147-75].

According to the experience with whole-body PET scanners, it seems that the sensitivity depends on lesion size: more than 90% for tumor sizes larger than 2 cm, but only around 25% for those smaller than 1 cm [Rosé C. et al. Nucl. Med. Commun. 2002; 23: 613-618]. These results may be significantly improved with the dedicated PET instrument proposed in this invention, specially the sensitivity to small tumors.

1.3 Motivations for a Partial-Body Camera Concept

Whole-body PET scanners are used clinically to diagnose and to stage a wide variety of cancers. Compared to whole body PET systems, dedicated partial-body equipment has potentially better spatial resolution, obtained with fine-grain crystal segmentation, and allows tighter coverage of the region under analysis, leading to a better sensitivity. Whole body PET system, because of their open geometry is also very sensitive to the background from the body, resulting in a lower target/background ratio. Moreover whole body PET systems are expensive and bulky.

Event counting sensitivity is an important parameter in PET, since when increased it allows a shorter examination time and lower injected dose, resulting on a lower radiation burden to the patient. Sensitivity depends on geometrical and physical parameters of the detector. The detector geometry should aim at solid angle coverage as large as possible, although some limitations are imposed by image reconstruction considerations as well as by the specifics of the human body anatomy and examination practice. The detector thickness and the crystal physical properties (density and composition) determine the photoelectric interaction probability for the emitted photons and in consequence have a direct impact on PET sensitivity.

On the other hand, the crystal length is responsible for the parallax effect in the image reconstruction process and the consequent degradation in position resolution. Parallax effect is an important issue especially when planar detectors located close to the object under examination are used. In consequence, we require high-density crystals combined with a method that provides depth of interaction information.

The ability to accumulate in a short time interval the event statistics needed for good image reconstruction depends on the performance of the data acquisition system. We require a data acquisition rate larger than 1 million events per second. This event rate corresponds, for example, to a total injected dose of 10 mCi, an uptake in the breast of 2% and a detector geometrical acceptance and efficiency as high as 10%. On the other hand, the detector will be subject to a large photon flux from decays occurring in the whole body. It is therefore important to reduce it as much as possible with a dedicated device, having a good acceptance for the organ under study, and a reduced acceptance for the rest of the body. Nevertheless is necessary that the data acquisition system to cope with a single photon background rate of the order of 10 MHz (2.5% of the total decays of 10 mCi dose). For these conditions, the combined efficiency of the readout electronics and data acquisition should be larger than 95%.

Under a large single photon background it is of paramount importance to achieve a very good time resolution to minimize accidental two-photon events. For the above-mentioned rates and for a photon time measurement r.m.s. of 1 ns, the background coincidence rate should be less than 30% of the true rate.

The number of events collected by unit time depends on the detector solid angle coverage. In the schematic layout where the ring diameter (Whole-body PET) or the separation between two plates (Partial-body PET) have a value D, the solid angle coverage varies with $D^{-2}$. If we consider, as an example, that whole-body PET has a ring diameter of D=60 cm and the two plates separated by D=10 cm, the solid angle coverage of partial-body PET is about 15 times that of whole-body PET, assuming a factor 2.5 loss due to incomplete angular coverage of the dual-plate configuration.

The dual-plate system of this invention has a spatial resolution of 1-2 mm which is about 5 times better than typical whole-body PET systems. We conclude that the significance to small tumors (~1-2 mm) in relation to whole-body PET is improved by a factor of the order of 10 due to better resolution and larger solid angle coverage.

2. STATE-OF-THE-ART

2.1 Parallel Plate PET Devices

In the past several parallel plate PET devices where proposed, in particular for positron emission mammography. One of the first exploratory papers on this subject, "Positron Emission Mammography (PEM): A Promising Technique for Detecting Breast Cancer", C. Thompson et al., IEEE Trans. Nucl. Sci Vol. 42, No4 (1995) 1012, discusses the motivations for Positron Emission Mammography. A PEM detector designed to fit into a conventional mammography unit is described based on the Hamamatsu R3941-5 position sensitive photomultiplier and on BGO crystals.

Computer simulations were carried out by various groups [e.g. the work described in "Dedicated PET scanners for breast imaging", R. Freifelder et al., Phys. Med. Biol. 42 (1997) 2463-2480] comparing designs of PET scanners dedicated to breast imaging with whole-body PET scanners. Performance estimators to compare the different designs, for example, the contrast, the standard deviation of the background and signal-to-noise ratios of reconstructed images. In general, the results of these simulations show that the dedicated scanners have better lesion detectability than a whole-body scanner.

The paper published in 2001, "maxPET: A dedicated mammary and axillary region PET imaging system for breast cancer", N. K. Doshi et al, IEEE Trans. Nucl. Sci Vol. 48 (2001) 811" and the Patent US Pub. No. 2001/040219 describe an apparatus and method for breast cancer, using LSO scintillator and a light guide coupling arrangement. This PET imaging system is based on two planar scintillator detectors, composed of arrays of scintillation crystals, photomultiplier tubes and light guides coupling the crystals to the photomultipliers. Compared to previous designs (e.g. U.S. Pat. No. 5,864,141), the light guides allow to improve the detector packing factor and consequently the detector sensitivity. However the light guides introduce important light losses. The coincidence timing resolution for the entire system is 8.1 ns. The estimated resolution in projection images is 4 mm.

These designs are based on photomultiplier readout. They do not provide a method of depth-of-interaction (DoI) measurement and are not sensitive to Compton events. As such the spatial resolution is affected by the well known parallax effect and the overall sensitivity is affected by the relatively low probability of both photons having photoelectric interactions (of the other of 25%). On the other hand, the above mentioned inventions address exclusively the photon detection principles. The loss of sensitivity due to dead time in the acquisition of data at high rates is not solved by these inventions. No method to select two photon coincidence events is described.

The measurement of DoI was soon recognized to be an important issue in planar detectors with large field of view and wide angular acceptance. The above mentioned designs based on photomultiplier readout do not provide a method to measure DoI. The work described in the publication "A room Temperature LSO/Pin Photodiode PET Detector Module that Measures Depth of Interaction", W. W. Moses et al., IEEE Trans. Nucl. Sci Vol. 42, No4 (1995) 1085, was among the first to propose a solution to provide DoI measurement in PET detectors. A detector module of pixelized crystals is readout by an array of PIN photodiode on one side and by a single PMT on other side. The DoI FWHM resolution is 4 mm at diode end and 13 mm at PMT end. This work showed that a double readout method could possibly provide DoI measurement, despite the poor performance achieved. Improved versions of the initial concept were since developed, like the PEM scanner described in "Development of the LBNL Positron Emission Mammography Camera", J. S. Huber et al, Proceedings IEEE Medical Imaging Conference, 2003.

The publication "ClearPEM, a dedicated PET camera for Mammography", P. Lecoq, J. Varela, Nuclear Instruments and Methods in Physics Research A 486 (2002) 1-6, describes the concept of a PEM system with DoI capability aiming at a large sensitivity. The detector uses the LuAP crystal as its basic component. This crystal has a density of 8.34 g·cm$^{-3}$ (compared to 7.4 g·cm$^{-3}$ for LYSO and 7.1 g·cm$^{-3}$ for BGO). However it has a light yield of about 10 photons/keV (compared to 27 photons/keV for LYSO and 9 photons/keV for BGO). The emission spectrum peaks at 365 nm and the signal has a time constant of 18 ns (compared to 40 ns for LYSO and 300 ns for BGO). The detector assembly is based on two detecting planes, each one formed by a certain number of crystal matrices (8×4 crystals). In total, the number of crystals is around 3000 per plane covering an area of about 10×12 cm$^2$. Depth-of-interaction information is obtained by the phoswich technique: instead of a single 20 mm long crystal, two 10 mm crystals are used with two different time constants. The signal shape allows distinguishing the longitudinal segments in which the interaction occurred. Alternatively, a method based on the readout of the front and back sides of the crystals was proposed in conjunction with two Avalanche Photo-Diodes (APD) to convert the crystal light into an electrical signal at both ends. The system requires low noise amplifiers and a high-degree of front-end electronics integration to achieve a compact system (64 amplification channels in a single chip). The highest signal is multiplexed to the chip output together with a channel identification binary code. A data acquisition system based on a fully synchronous architecture is proposed. The present invention is the result of investigation triggered by this early exploratory work.

The possibility of combining PEM detectors with biopsy devices was first demonstrated in publication "An Apparatus for Positron Emission Mammography Guided Biopsy", Raylman et al., J. Nucl. Med., 42 (2001) 960. The PEM system consisted of a two square (10 cm×10 cm)-detector arrays of discrete (3 mm×3 mm×10 mm) blocks of GSO crystal. The scintillation light was collected by arrays of position-sensitive PMTs. The detector heads were mounted 18 cm apart on a Lorad stereotactic biopsy table. Despite the fact that the PEM detector did not bring at the time any important innovation, the integration with a commercial biopsy system was a relevant landmark.

Various exploratory works tried in the past to replace the standard or the position sensitive photomultipliers normally used in PET detectors to convert the scintillation light, by some type of semiconductor photosensor. Semiconductor sensors are substantially smaller, potentially cheaper and are immune to magnetic fields making them potentially suitable for PET and MRI co-registration. The papers "A Novel APD-Based Detector Module for Multi-Modality PET/SPECT/CT Scanners", A. Saoudi et al., IEEE Trans. Nucl. Sci Vol. 46 (1999) 1089, and "A prototype high-resolution animal positron tomograph with avalanche photodiode arrays and LSO crystals", Ziegler et al., European Journal of Nuclear Medicine and Molecular Imaging, Volume 28, Number 2 (2001) 136-143, both describe small prototype devices that combine crystal scintillators with avalanche photodiodes (APD).

While providing an elegant path to compact PET systems, APDs have their own drawbacks. Most important is the much lower gain relative to photomultiplier. This fact implies the use of state-of-the-art low noise amplification electronics, which is a problem for imaging systems larger than prototypes with a few channels. On the other hand, due to the pixelized nature of photodiodes, the total number of readout channels grows quadratically with the detector dimensions, whereas position sensitive photomultipliers only grows linearly. This implies the need of high performance data acquisition electronics systems to build high sensitivity, large field of view PET scanners based on avalanche photodiodes. It became clear that the extensive use of APDs is PET systems with a large number of channels requires new developments in the electronics systems. The innovations introduced by our work answer in particular this issue.

More recently, the Patent US Pub. No. 2003/0105397 describes a readout electronics scheme for high resolution, compact PET imagers based on LSO (lutetium ortho-oxysilicate) scintillators and avalanche photodiodes (APD) arrays. The readout is based on a multichannel ASIC (Application Specific Integrated Circuit) for the LSO/APD arrays for application to breast cancer diagnosis. The circuit uses a transimpedance amplifier input stage and uses leading edge discriminators for timing pick-off. Results obtained with a discrete electronics prototype report a time resolution of 3.6 ns FWHM. Depth of interaction is obtained by readout of both ends of the LSO crystal and a resolution of 2.5 mm FWHM is reported.

The ASIC circuit is the crucial part of this work, aiming at a compact PET system with a large number of channels. The work was concentrated on a fast front-end amplifier compatible with the fast rise time of the APD signals. For trigger purposes the ASIC uses a classical leading edge discriminator, which provides limited time accuracy due to the time walk associated to pulses of different amplitude. This solution has several drawbacks. The time resolution is dependent of the amplitude range of the signals (larger amplitude dynamic range implies larger discriminator time-walk), which obliges to limit the amplitude dynamics to preserve the time resolution compatible with a low rate of random coincidence two-photon events. But limiting the amplitude dynamics implies to reduce the front-back signal excursion and deteriorating in consequence the DoI resolution. It also implies that Compton events with multi-hits of different energy deposits will be badly measured. Finally, patent US Pub. No. 2003/0105397 does not address the problem of data acquisition nor proposes an architecture capable to keep high sensitivity at high rates.

2.2 Electronics and Data Acquisition in PET Systems

The electronics and data acquisition systems are part of the complex process that leads to the final image. It starts with the interaction of radiation in the human body, followed by the physics processes involved in the detection of particles and in the generation of the corresponding electrical signals. The electronics systems are then responsible for the analog processing of the detector electrical signals, usually amplifying the detector pulses and converting the analog signal to a digital representation. The trigger system is in charge of identifying the occurrence of particle interactions in the detector (events) preparing the stage for the data acquisition process. The data acquisition system will then collect the digital data, selecting on the flight the relevant information. Finally these data are transferred to a data acquisition computer where it is stored in a permanent medium (hard disk or magnetic tape).

The stored data files contain a list of events (list-mode), and for each one a record of the detected particles and its properties (coordinates, time, energy, etc.), or pre-processed information in a format suitable for the image reconstruction process (e.g. sinograms).

Modern medical imaging systems tend to have a large number of individual sensors (crystals, pixels, etc.) in an attempt to improve the image spatial resolution. Each elementary sensor is associated to analog front-end electronics forming a detection channel. The number of channels varies substantially from device to device, however it reaches today values of the order of ten thousand.

The data acquisition system has been a limiting factor of the efficiency of medical imaging systems [J. Varela, Electronics and Data Acquisition in Radiation Detectors for Medical Imaging, Nuclear Instruments and Methods in Physics Research A 527 (2004)21-26], constraining the maximum event rate. In order to minimize the dose given to patients and to reduce the examination delays, a substantial increase in the efficiency of these systems is required. Present designs require the ability to handle trigger rates of the order of 1 million events per second and data rates up to 500 Mbyte/s. This performance should be achieved without loss of efficiency due to dead time effects. These requirements are not easy to fulfill and in consequence the performance of medical imaging is still relatively poor.

The efficiency of data acquisition systems is affected by dead time of various origins. We define dead time as the time during which the system cannot accept and record new events. There are essentially three sources of dead time. The first is the time the sensor and the associated electronics take to create the electrical pulses. The second source of dead time is the analog to digital conversion. When charge integration ADCs are used, the dead time per conversion is of the order of 100 μs, which may represent a serious limitation. Finally, the time the system takes to execute the trigger algorithm and to read the digital data, clearing the local memories for the next event, is usually the most important source of dead time.

The relative dead time is given by:

$$D = 1 - e^{-R\delta} \quad (1)$$

where δ is the absolute dead time per event and R is the real rate. The data acquisition rate is given by:

$$A = R \cdot e^{-R\delta} \quad (2)$$

If the product R·δ becomes equal to 1 the acquisition rate is only 37% of the real rate. Above R·δ=1 the acquisition rate decreases even if the real rate increases.

3. SUMMARY OF THE INVENTION

This chapter summarizes the description of a complete PET imaging system dedicated to exams of body parts such as the breast, axilla, head, neck, liver, heart, lungs, prostate region, and body extremities. In particular the device is intended to the detection and follow-up of various types of cancers in various parts of the human body.

The system can also be used to produce functional images of the interior of human body parts, based on the affinity of specific molecules marked with a positron emitter to certain regions, organs, tissues, activity or functions of the human body.

The imaging system may also be used to make PET exams of small animals.

Different innovative aspects are combined and articulated to provide improved imaging performance in relation to previous systems or proposals.

3.1 System Description

The partial-body PET system is composed of:
- a PET detector formed by two or more detecting plates (detector heads) with dimensions that are optimized for the breast, axilla region, brain and prostrate region;
- Motorized mechanical means to allow the movement of the plates under computer or manual control allowing taking data in several orientations as needed for tomographic image reconstruction;
- An electronics system composed by the front-end electronics system, located physically on the detector heads and the trigger and data acquisition system located off-detector in a crate system;
- Data acquisition and control software;
- An image reconstruction and analysis software that allows reconstructing, visualizing and analyzing the data produced during operation.

3.2 Device Configuration

The detector plates are able to rotate around the PET axis, under computer control, allowing taking data in several orientations as needed for tomographic image reconstruction.

The PET detector system can rotate by 90° allowing exams in two different configurations, such that the rotation axis, mentioned above, is either horizontal or vertical.

The motorized mechanical system allows the movement of the plates under computer or manual control. Other movements are possible, namely a vertical movement, allowing the adjustment of the plates height, an horizontal movement, allowing the adjustment of the plates position, rotation of the PET plates around the PET axis, allowing tomographic image reconstruction, and rotation of the PET system by 90°.

3.3 Integration with Other Systems

The partial-body PET of this innovation allows for an easy integration with a digital Computer Tomography (CT) system or an optical imaging system providing images of the body part under investigation that can be merged with the PET images.

The partial-body PET can also be combined with a stereotatic biopsy system in particular in the case of breast exams.

3.4 Innovation

The PET system concept of this invention integrates the following innovative aspects:

1. A new partial-body PET system based on two or more detector plates (detector heads), suitable for integration with CT, optical imaging or stereotatic biopsy, characterized by high sensitivity and excellent resolution as consequence of the innovative aspects described below.
2. The ability to detect and use in image reconstruction about 75% of the events where at least one of the two PET photons has Compton diffusion in the detector, by identifying individual photon interactions (photoelectric or Compton). The so-called Compton events, which represent about 70% of the total number of events, are normally discarded in PET system. By recovering a high fraction of Compton events, the present system allows to increase the sensitivity by a factor 3 in relation to systems that are only sensitive to photoelectric events.
3. The measurement of the coordinates of the photon interaction point in the detector with a precision of the order of 1 mm in the three space directions, by using fine-grained crystal granularity and a method for measuring the third coordinate (DoI—depth-of-interaction) based on the sharing of scintillating light at the two ends of the crystal pixels, allowing a spatial resolution of the reconstructed images of the order of 1 mm.
4. A detector head that integrates in a compact mechanical system a large number of LYSO crystal pixels (few thousand) each with dimensions of the order of 2×2×20 mm³, two photosensors (avalanche photodiodes) per crystal pixel capable to detect the scintillating light on both crystals ends and one electronics amplification channel per photosensor.

5. A new electro-mechanical system allowing the computerized control of the detector plate movements according to the description in section 3.2.

6. A new data-driven and synchronous architecture for front-end analog signal processing, which includes low-noise amplification, signal sampling, analog pipeline storage, event detection, and output multiplexing, operating in pipeline mode with fixed latency at frequencies of the order of 100 MHz. This architecture is implemented in front-end chips located in the detector heads. The output multiplexing stage selects two channels allowing good efficiency for Compton events.

7. A new architecture for on-line measurement of the photons detection time based on the analog-to-digital conversion of detector pulse samples, and on the digital computation of the pulse time. The precision on the PET two-photon coincidence is of the order of 0.5 ns allowing maintaining the random coincidence noise at a low level. The time measurement algorithms are executed by digital electronics implementing a pipeline architecture operating at high frequency which does not introduce dead time in the data acquisition process.

8. A new architecture of the trigger and data acquisition system capable to operate at a rate of one million PET events per second with an efficiency better than 95%, for a background photon interaction rate of 10 million photons per second. The architecture is based on the combination of a pipelined synchronous section followed by a dual-bus asynchronous readout system.

4. DESCRIPTION OF DRAWINGS

FIG. 1 Mechanical system configuration for breast exam (left). Mechanical system configuration for axilla exam (right).

Figure 2:
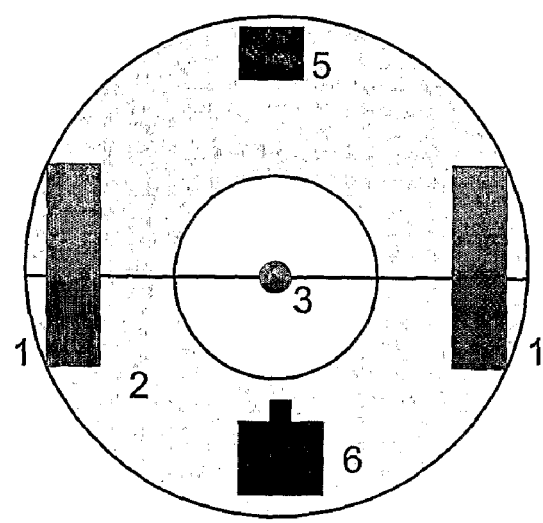

FIG. 2—Integration of Computer Tomography system with partial-body PET (top view).

Figure 3:
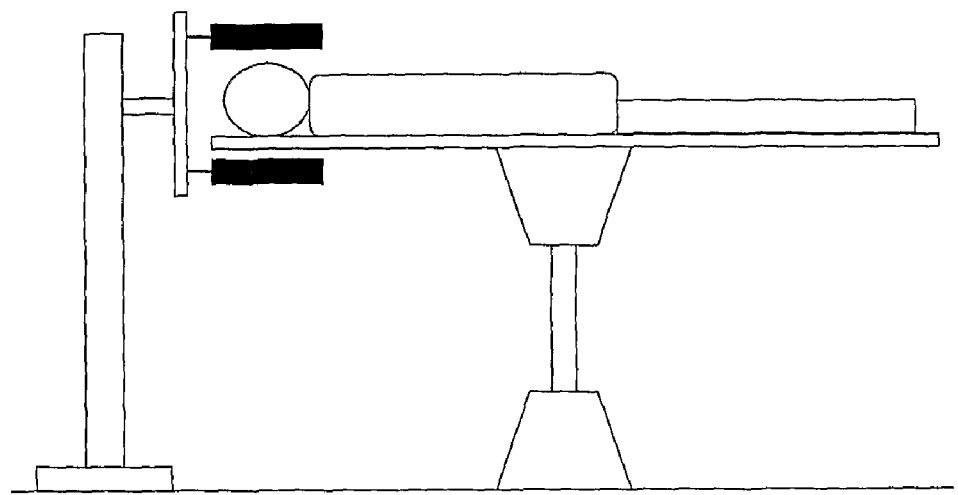

FIG. 3—PET-CT system configuration for brain exam (for simplicity only the PET detector heads are represented).

Figure 4:
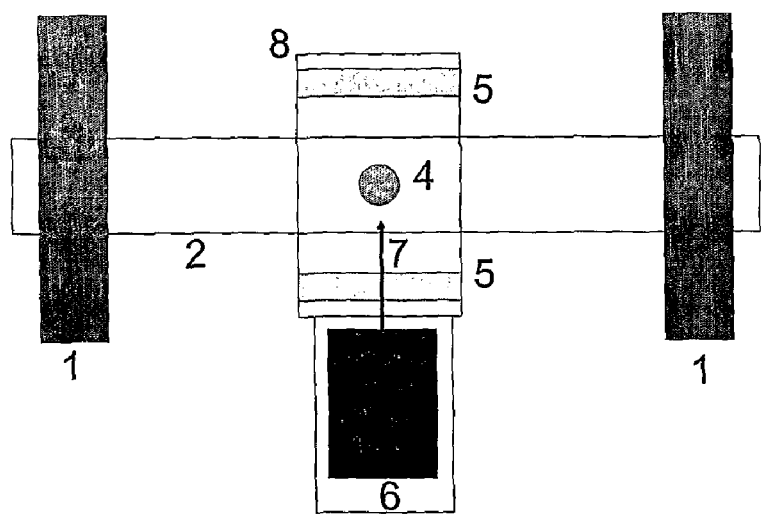

FIG. 4—Integration of stereotatic biopsy with partial-body PET (top view).

Figure 5:
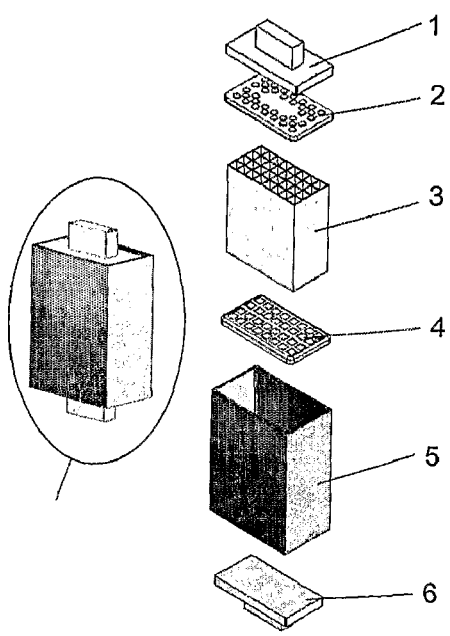

FIG. 5—Detector module components and assembly principle.

Figure 6:
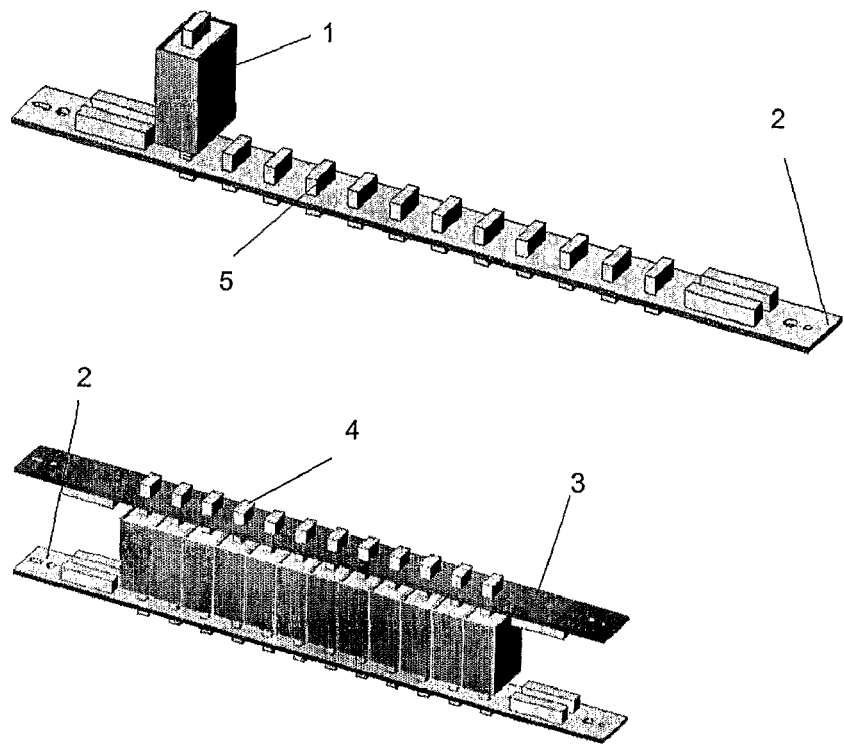

FIG. 6—Supermodule of 12 modules.

Figure 7:
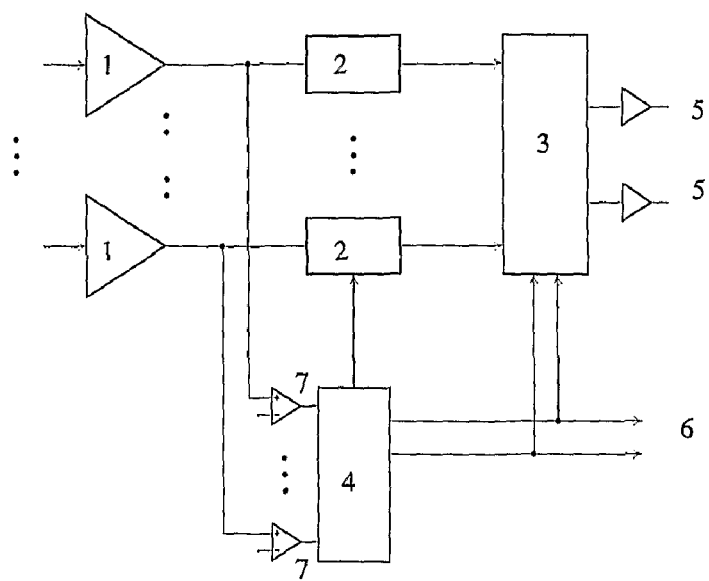

FIG. 7—Architecture of the front-end chip.

Figure 8:
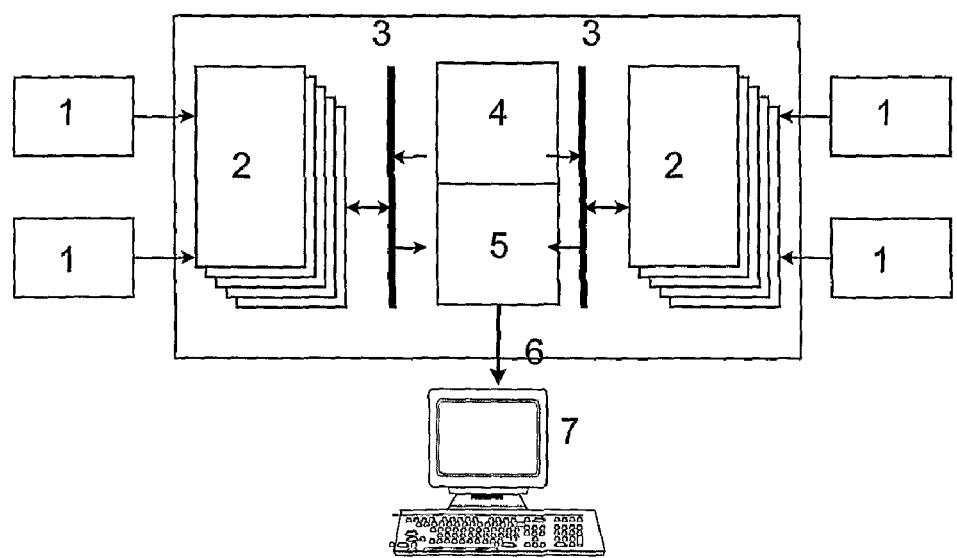

FIG. 8—Architecture of the trigger and data acquisition electronics.

Figure 9:
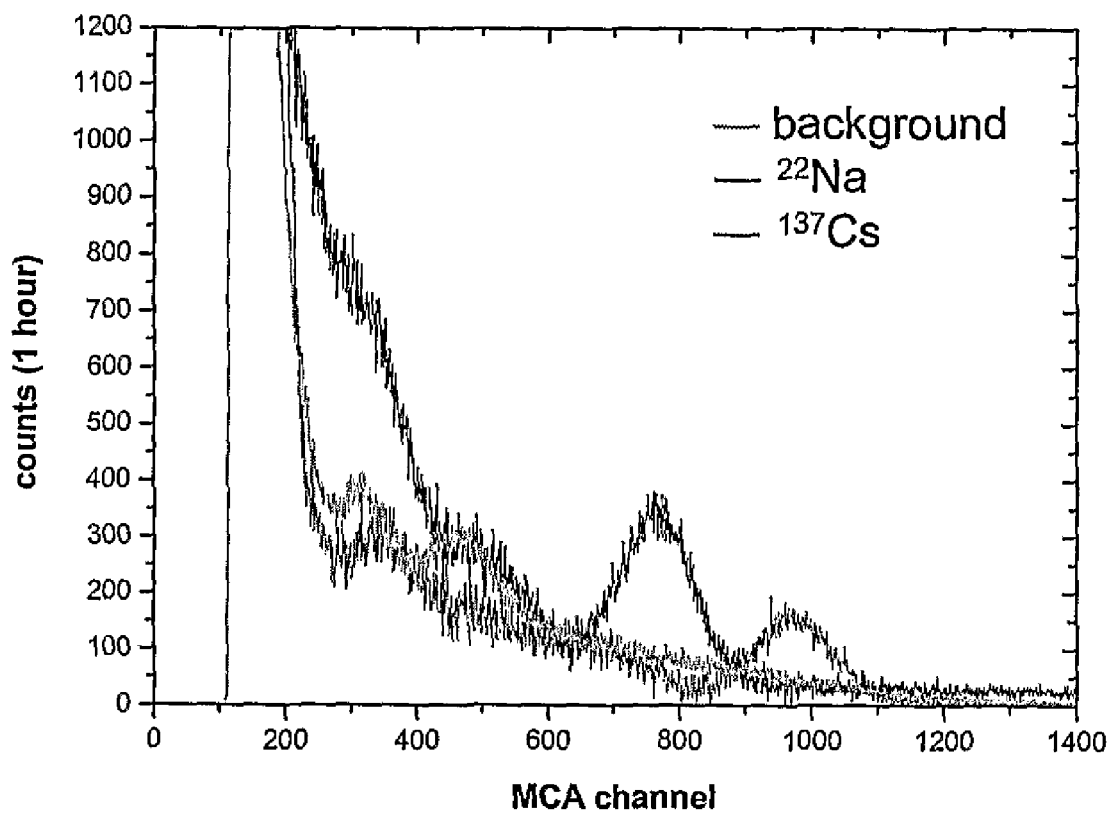

FIG. 9—Energy spectrum of photons detected in a LYSO crystal matrix with S8550 APD readout, at the temperature of 20° C.

Figure 10:
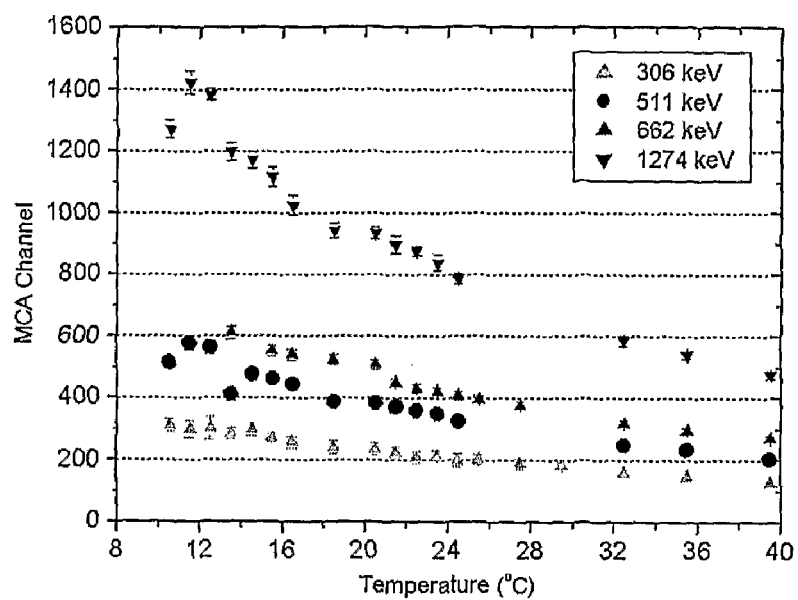

FIG. 10—Temperature dependence of the photopeak position.

Figure 11:
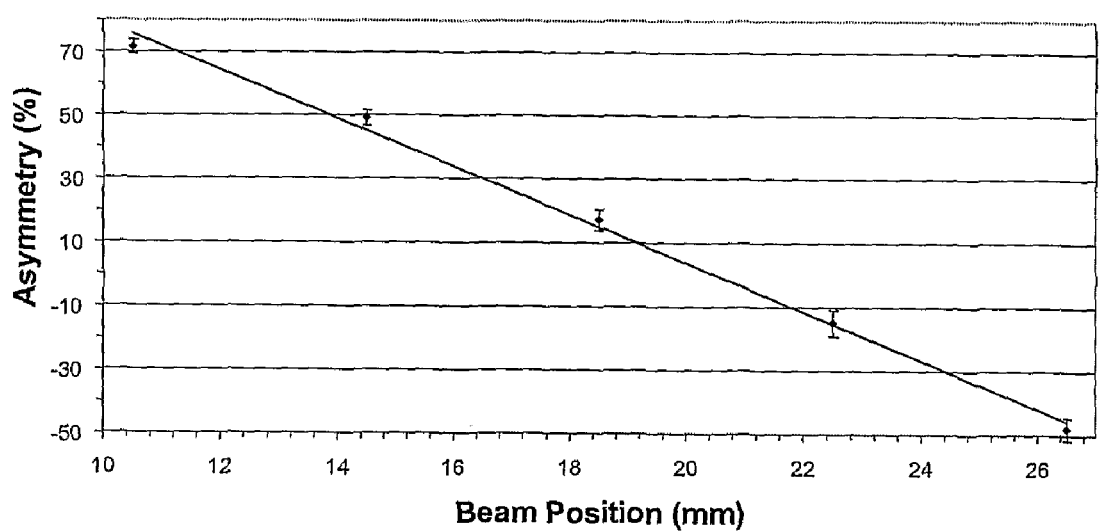

FIG. 11—Asymmetry between the light outputs at the two crystal faces as a function of the photon beam interaction point.

Figure 12:
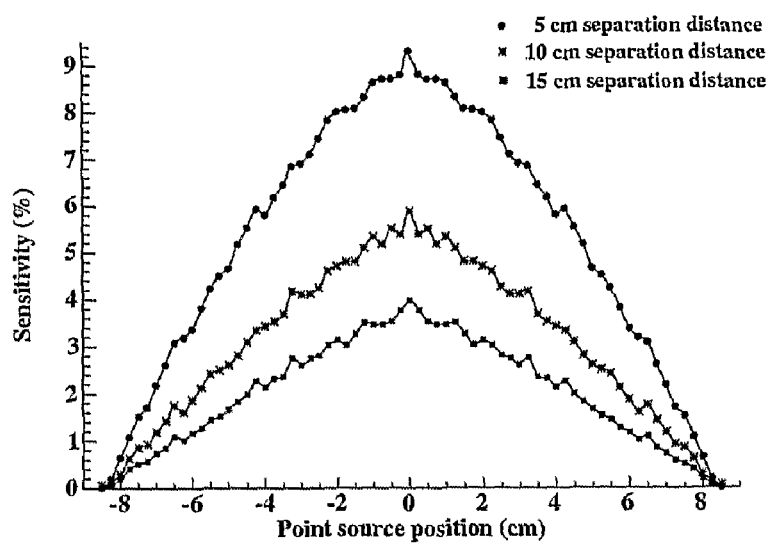

FIG. 12—Sensitivity profiles along the axis in the central plane of the FoV for different separation distances between the detector heads.

Figure 13:
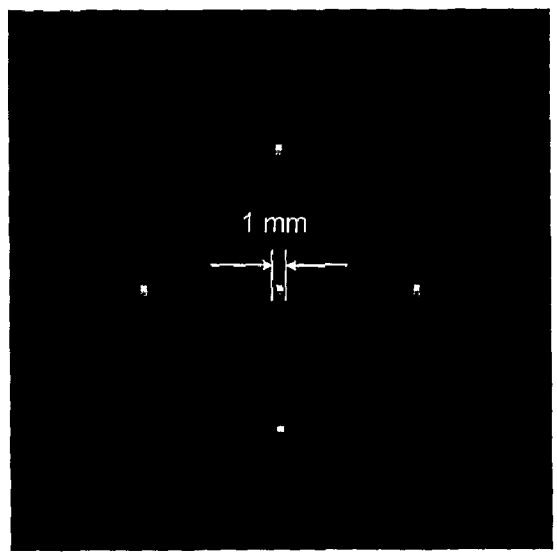

FIG. 13—Transaxial central plane of the reconstructed image of the cross-phantom.

5. DESCRIPTION OF THE INVENTION

This chapter describes a complete PET imaging system dedicated to exams of body parts such as the breast, axilla, head, neck, liver, heart, lungs, prostate region, and other extremities. The imaging system may also be used to make PET exams of small animals. One of the main characteristics of the present system is how different innovative aspects are combined and articulated to provide improved PET imaging performance in relation to previous systems or proposals.

5.1 The Partial-Body PET System

Device Configuration

The partial-body PET system has the following geometrical configuration:

a) The PET detector is formed by two or more detecting plates (detector heads) with dimensions that are optimized for the breast, axilla region, brain and prostate region.

b) The plates are able to rotate around the PET axis, under computer control, allowing taking data in several orientations as needed for tomographic image reconstruction.

c) The PET detector system can rotate by 90° allowing exams in two different configurations, such that the rotation axis mentioned in b), is either horizontal or vertical.

FIG. 1 shows a schematic representation of the PET system in position for breast exam and axilla exam.

The detecting plates (1) (detector heads) form the PET detector itself. The separation distance between the plates (1) can be adjusted under operator control. For safety reasons, a minimum separation between the plates is built-in.

The motorized mechanical system allows the movement of the plates (1) under computer or manual control. The following movements are possible:

Vertical movement, allowing the adjustment of the plates height;

Horizontal movement, allowing the adjustment of the plates position;

Rotation of the PET plates (1) around the PET axis, allowing optimizing tomographic image reconstruction;

Rotation of the PET system by 90°.

Integration with Computer Tomography (CT)

The partial-body PET of this innovation allows for an easy integration with a digital Computer Tomography (CT) system. The concept is represented in FIG. 2. The base (2) allows the installation of the partial-body PET detector heads (1), as well as an X-ray source (6) and an X-ray detector (5). The rotation of system around the axis (3) under computer control allows acquiring simultaneously PET and CT data at different angles as required for tomographic image reconstruction.

This combination is particularly interesting for examining the brain. The mechanical system configuration is such that the PET and CT detectors (1) can rotate around the head (FIG. 3). The two images reconstructed from the PET and CT data can be merged in a single image that provides simultaneously functional and structural information.

Integration with Optical Imaging System

The partial-body PET system can be integrated with an optical imaging system providing images of the body part under investigation that can be merged with the PET images. The 3D optical image is reconstructed from several photographs taken by video cameras placed at locations (5) and (6) of FIG. 2. The two cameras have complementary orientations in the plane that contains the rotation axis. Different pictures taken at different angular orientations along the rotation allow for a 3D reconstruction of the external skin surface. Ink marks on the skin are visible on the optical image. After merging with the PET image, these marks provide references that makes surgery intervention easier, in case the removal of a tumor is required.

Integration with Stereotatic Biopsy

If necessary the clinician should have the possibility to biopsy the region detected as malign in the PET image. The best accuracy is obtained with a stereotatic biopsy system guided by the PET image: the coordinates of a given point, selected on the PET image, are transmitted to the stereotatic controller which moves automatically the needle tip to the required position.

The system described in this invention includes the capability to be easily integrated with an automatic biopsy device. The biopsy device is fixed to the PET system as indicated in FIG. 4. The partial-body PET detector heads (1) are fixed to its base (2). The distance between detector heads can be adjusted. The base (2) can rotate around the axis (4).

The biopsy system is composed of the base (8), the needle control system (9), the needle (7) and the fixation parts (10). The needle control system (9) controls the displacements of the needle (7) positioning the needle tip in a predetermined space point. The fixation parts (10) can move along the main axis of the base (8) and are used to compress and immobilize the body part under investigation.

The biopsy system is integrated with the partial-body PET system through the rotation axis (4). The two systems are able to rotate independently. The rotation control system determines automatically the angular relation between the two systems. This angular displacement is the only parameter needed to transform the coordinates from the PET system into the coordinates of the biopsy system. The biopsy control system (9) should be easily detachable from the base (8) in order to allow the PET detector heads (1) to rotate around the fixation parts (10) to form a PET image of the compressed and immobilized body part.

The integration of PET with stereotatic biopsy is particular interesting in the case of breast exams.

In this case, the following clinical sequence is followed:
a) The complete examination sequence (two breast and two axillas) is performed. Full image reconstruction may proceed in parallel. Shortly after the end of the sequence (about 5 nm) the breast images are available.
b) In case a biopsy is found to be needed, the patient is positioned again to exam the relevant breast, reproducing the breast positioning of the previous exam as much as possible (ink markers may be used). Because the tumor location is already known, it is possible to define a reduced region (with an accuracy of the order of 1 cm) were image reconstruction is done. This procedure should allow reducing considerably the waiting time. Once the tumor location is visible on the PET image the biopsy may be done bringing in position the biopsy control system (9).

It is clear that the biopsy should be done without removing the breast fixation parts. On the other hand, the needle incident direction should be the same as the compression direction to guarantee that the tumor is not displaced by the needle impact.

The fixation parts have holes allowing the needle passage. On the other hand, the biopsy system may perform angular adjustments of the needle incident direction. The breast fixation parts together with the capabilities of the biopsy system allow the needle tip to reach any point within the breast volume.

5.2 The PET Detector Concept
Photon Detection and Measurement

The photon detector is based on high-density scintillating crystals (Cerium doped Lutetium Yttrium Orthosilicate (LYSO)), with dimensions 20×2×2 mm. The crystal transverse dimensions (2×2 mm$^2$) are determined by the desired spatial resolution, whereas the longitudinal dimension (20 mm) is dictated by the required detector sensitivity.

The probability that two 511 keV photons undergo photoelectric interactions is only 30%. Therefore there is a strong motivation to recover, at least partially, the Compton interactions. The PET system here described is sensitive to Compton scattering followed by photoelectric interaction, identifying and reconstructing events with two-hit photons with 75% efficiency.

The hit energy is given by the sum of the crystal pulse amplitudes after channel calibration. The hit longitudinal coordinate is extracted from the relative amplitude of the pulses at both crystal ends, using an algorithm that depends on the light collection properties of the optical system. The hit time is deduced from a measurement of the pulse phase relative to the system clock.

Double hit Compton events are recovered by identifying two hits in coincidence in a detector plate, compatible with a total energy of 511 keV. An algorithm based on the kinematics of the Compton diffusion is used to identify the hits to the Compton diffusion or to the photoelectric interaction. The identification is done with high efficiency (of the order of 90%).

The present PET device is designed to have a photon time measurement r.m.s. of 500 ps for 511 keV photons, which is crucial to minimize accidental two-photon events.

Sensitivity and Geometrical Configuration

The detector geometry aims at large solid angle coverage of the region under analysis, within the limitations imposed by the specifics of the human body anatomy and examination practice. The detector thickness and the LYSO crystal physical properties (density and composition) determine the interaction probability for the emitted photons and in consequence have a direct impact on the sensitivity. We achieve a sensitivity for two-photon events of 40 cps/kBq in the center of the Field Of View (FOV) for 10 cm inter-plate distance.

In general, the crystal length is responsible for the parallax effect in the PET image reconstruction process and the consequent degradation in position resolution. Parallax effect in PET systems is an important issue especially when planar detectors located close to the object under examination are used. In consequence, we combine the use of high-density long crystals to maximize sensitivity with a method that provides depth of interaction information. By measuring individual photon interaction points with accuracy of the order of 1 mm in all space direction we eliminate the parallax effect.

Signal Processing

The present PET system uses avalanche photo-diodes (APD) to convert the crystal light into an electrical signal. Avalanche photo diodes have a number of advantages over position-sensitive photomultipliers, namely higher quantum efficiency, better lateral uniformity and less inter-channel cross talk. On the other hand they allow the construction of very compact detector assemblies, allowing in particular the double readout scheme used for DoI measurement. The interaction probability of photons in the APDs and associated electronics is estimated at a few percent. On the other side, the APD gain is lower that the PM gain, which implies the use of low-noise preamplifiers. The noise specification of the charge amplifier is a function on the energy and time resolution requirements. The total charge at the preamplifier input for a 511 keV photon depositing its energy in a LYSO crystal is around 30 fC (maximum value). An equivalent noise charge (ENC) of around 1000 e$^-$ r.m.s. contributes less than 2% to the r.m.s. energy resolution at 511 keV. For a signal peaking time of 30 ns, this noise level implies a time resolution of the order of 0.5 ns as required.

A high-degree of front-end electronics integration is needed to achieve a compact system. Low power consumption is also an important specification. We are presently designing a front-end chip that integrates 192 channels. The chip performs signal amplification and selects the two highest signals to be transmitted to two outputs. Two output digital lines provide the identifications of the selected channels.

The output multiplexing is a source of inefficiency due to pile-up of signal events with background photons. However this inefficiency is kept at a low level because of the fast signals produced by the LYSO crystals. The pile-up probability is of the order of 6%.

Trigger and Data Acquisition Principles

The efficiency of the data acquisition system is significantly improved in relation to available PET systems, due to an innovative architecture based on multi-event storage and pipeline trigger processing. Sampling ADCs provide input streams of digital data to the trigger system. The trigger algorithm is decomposed in a sequence of elementary operations that are executed in pipeline mode.

The pipeline digital trigger allows implementing complex trigger algorithms without introducing dead time. In parallel to the trigger pipeline processing, data is continuously stored in memories at clock rate, waiting for the trigger result. When a trigger signal is present, the selected data are transferred to a second memory where it waits to be read-out. The second memory is organized as a multi-event buffer in order to handle Poisson fluctuations of the event rate.

Partition Between on-Detector and Off-Detector Electronics

In our design the on-detector electronics includes the amplifier and analog multiplexing circuits, as well as the analog-to-digital converters.

To transmit the signals from the detector heads, digital serializers are used to minimize the number of lines connecting to the trigger and data acquisition system. The off-detector system includes the trigger and data acquisition cards implemented in a crate system.

This solution allows for a relatively simple integration of the electronics in the detector heads mechanical design and is compatible with a simple cooling system to remove dissipated heat. It allows the design of compact detector plates, which are required in a flexible movable system. The need for detector movements (e.g. detector rotations) creates constrains on the amount of cables that connect the detector head to the data acquisition system. In our architecture, this problem is solved by introducing an analog multiplexing stage that reduces the number of channels.

5.3 Partial-Body PET Capabilities

Generic Capabilities

The partial-body PET system described here has the following generic clinical capabilities:

1) The PET system allows to exam localized body regions (e.g., breast, axilla, brain, prostate region, etc.).
2) The PET system allows to exam small animals.
3) The exam produces 3D tomographic images, capable to guide chirurgical intervention or automatic stereotatic biopsy system.
4) The image spatial resolution is of the order of 1 mm in the three space coordinates. This parameter determines the precision in localizing lesions with the technique.
5) The detector is designed so that the scanner is sensitive to small tumors (order of 1 mm), as long as the FDG uptake matches the detector sensitivity and overcomes the background noise.
6) The partial-body PET system can be integrated with a stereotatic biopsy system driven by the PET images.
7) The partial-body PET system can be integrated with X-ray computer tomography or optical imaging systems for image co-registration.

Performance Parameters

In the following we summarize the performance parameters of the partial-body PET system:

1. The dedicated partial-body PET system of this invention allows examining specific regions of the human body or animals with high sensitivity (up to 100 cps/kBq) and good spatial resolution (order of 1 mm).
2. The system optimizes the detection sensitivity (fraction of accepted two-photon events) in order to reduce the injected dose and the examination time needed. In the case of breast cancer, this is particularly important in determining the frequency of scans for women.
3. The device sensitivity for two-photon events from the breast is 40 cps/kBq in the center of the Field Of View (FOV) when the PET plates are 10 cm apart.
4. The PET detector is subject to a large radiation field due to the activity deposited in the body outside the region under analysis. This radiation is responsible for background events (random coincidences) that affect the image quality and deteriorates the resolution. The PET system reduces this background to a level below 20% of the true rate in the worst conditions.
5. The PET system is designed to stand a true coincidence rate up to 1 MHz and a total single rate up to 10 MHz, without significant deterioration of the detector counting sensitivity.
6. The PET system is designed so that the scanner is sensitive to small tumors (1 mm) with a statistical significance above 3, with a data acquisition time of the order of 1 nm, assuming an injected dose of 10 mCi and a ratio of FDG absorption between lesion and normal tissue equal to 3, provided that the exam can de done with the detector heads 10 cm apart.

5.4 The Detector Heads

The PET imaging system is based on two parallel detector heads each one holding a certain number of detector modules. Prototypes under construction will have 96 modules per detector head.

Detector modules are units providing 32 detector crystals optically isolated in a 4×8 arrangement, coupled to APD arrays at both ends. Crystals and APD arrays are enclosed in a plastic mechanical assembly. Detector modules are mechanically stable units suitable for integration in larger detector structures.

Crystals

The basic components of the PET system are LYSO (5% Yttrium) crystals. The LYSO crystal has a density of 7.4 $g \cdot cm^{-3}$ and a light yield of about 27 photons/keV. The emission spectrum peaks at 430 nm and the signal has a time constant of 40 ns.

The lateral crystal surface is slightly polished in order to optimize the gradient of light sharing with impact position necessary for a measurement of DoI with good resolution.

Photosensors

The PET system uses Avalanche Photo-Diodes (APD) to convert the crystal light into an electrical signal. APD arrays of 4×8 diodes are available from Hamamatsu (S8550). A new package for this device (S8550-SPL) was designed and produced specifically for this application. The pixel effective size is 1.6×1.6 $mm^2$, compatible with the planned crystal transverse size. The quantum efficiency of this device at the LYSO emission peak is about 75%. The APD gain is around 50, the dark current is of the order of 2-4 nA and the terminal capacitance is 9 pF.

The APDs systems operate at a bias voltage of 360-400 V. The gain has a temperature gradient of −2.4%/oC which implies that the system has to operate under stabilized thermal conditions.

Detector Head Mechanics Integration

Represented with the reference (17) a schematic representation of the detector module is shown in FIG. 5. Each detector module is composed by a 4×8 lutetium yttrium oxyorthosilicate (LYSO:Ce) crystal array. The crystals have a 2×2 mm$^2$ cross-section and 20 mm in length and are optically isolated by a 250 μm wrapping. The wrapping provides the crystal support and enclosure (13), defining volumes of size 2×2×20 mm where individual crystals are inserted, and provides the diffuse reflecting surfaces needed to optimize the crystal light collection.

Each side of the crystal matrix is optically coupled to a 32-pixel Hamamatsu S8550-SPL APD array (2 and 4) for DoI measurement. The APD array is mounted in a small PCB (11 and 16) equipped with a temperature sensor. The components of a detector module are housed and sealed in a dedicated plastic mechanical assembly (15) with a mechanical precision of 0.1 mm. Each module has external dimensions of about 12×20×35 mm. Each module has a 40-pin connector in each side.

Depending on the implementation, 12 or 24 detector modules are mechanically fixed and electrically connected to front and back electronics PCBs, forming a supermodule. The principle of supermodule assembling (12 modules) is illustrated in FIG. 6. The detector modules (17) are mounted in connectors (18) in the front-end printed-circuit board PCB (19). A second PCB (20) closes the supermodule. The electronics chips (21) are mounted on the external face of the two PCBs. Connectors for cables linking to the data acquisition system are also mounted in the PCBs.

Four supermodules, each with 24 modules, are mounted together forming a detector plate. The packaging fraction for the detector, defined as the ration between the crystal volume and the volute of the detector plate, is of the order of 52%. A container box integrates the detector plate, the auxiliary electronic card and the cooling components forming a detector head.

5.5 The Electronics and Data Acquisition Systems

The front-end and data acquisition electronics systems are crucial components of the partial-body PET system. The performance of these electronics systems is determinant to achieve high detection sensitivity and low random background noise, without compromising the spatial resolution allowed by fine segmented crystals.

The front-end system is based on a data-driven synchronous design that identifies and multiplexes the analog signals of channels above threshold. The off-detector system receives digitized data streams, applies a coincidence trigger based on the computation of the detector pulses amplitude and timing, and collects the data into the data acquisition computer. To minimize deadtime, the architecture makes extensive use of pipeline processing structures and of de-randomizer memories with multi-event capacity. The system operates at input clock frequency 100 MHz and is able to sustain a data acquisition rate of one million events per second with efficiency above 95%, under a total single photon background rate in the detector of 10 MHz. These parameters were defined such that the electronics and data acquisition systems are not the limiting factor of the PET sensitivity for the applications foreseen.

The basic component of the front-end system is a low-noise amplifier-multiplexer chip presently under development. The off-detector system is designed around a dual-bus crate backplane for fast intercommunication among the system modules.

In summary the main capabilities of the system are the following:
1) Data acquisition rate larger than one million events per second.
2) Ability to sustain a single photon background rate of the order of 10 MHz.
3) For the above conditions, the combined efficiency of the readout electronics and data acquisition is larger than 95% for photoelectric events.
4) The analog front-end electronics characteristics (signal shaping, noise, digital conversion) allows a time resolution in the photon measurement of 500 ps r.m.s., for 511 keV photons.
5) The system layout is compatible with compact and movable detector plates, minimizing electronics and connectors on the detector and interconnecting cables.

The PET electronic system and data acquisition is composed by two main systems:
1) The Front-End Electronics System, located physically on the detector heads, performs signal amplification, channel selection and analog multiplexing, as well as analog to digital conversion.
2) The Trigger and Data Acquisition System, located off-detector in a electronics crate system, performs temporary data storage, trigger computation, data selection, and data transfer to the acquisition computer.

Front-End Electronics System

The front-end system is composed of Front-End Boards (FEB) providing an interfacing directly with the detector modules, and a Service Board for clock distribution, power supply distribution, bias voltage regulation and temperature monitoring. Each FEB corresponds to a certain number of crystal modules depending on the application (24 modules in the present design). The FEB includes:
1) Front-end integrated circuit chips with 192 channels operating in pipeline mode at high frequency with fixed latency. The circuit performs low-noise amplification, shaping of the APD signals, analog pipeline storage, pulse detection and output multiplexing. The output multiplexing selects two channels above a given threshold together with channel identifiers allowing good efficiency for Compton events.
2) Analog-to-digital (ADC) converters followed by parallel-to-serial converters and digital line drivers.
3) Connectors for output digital signals, control and clock lines, for distribution of low voltage and APD bias voltage, and for reading the temperature sensors.

FIG. 7 shows the front-end chip architecture. The amplifiers (1) specifications are:
1) Maximum input charge 30 fC
2) Input ENC below 1000 e$^-$.
3) Power dissipation below 3 mW per channel.
4) Radiation tolerance up to 5 krad total dose.
5) Output signal shaping with peaking time of 30 ns.

A multiplexer is used to collect in two chip outputs (23) the signals above a given threshold, reducing the connections to the data acquisition system. The multiplexing circuitry has the following components:
1) Sample and hold circuits (22) working at a clock frequency.
2) Capacitor arrays (24) storing the charges of the pulse samples.
3) Comparators (27) followed by digital logic (28) to determine the channels above threshold.

4) Multiplexer circuit (29) connecting the inputs to two analog (23) and to two digital outputs (30).

Trigger and Data Acquisition System

The Trigger System and Data Acquisition (Trigger/DAQ) is responsible for identifying the interesting two-photon events and to store the event data in a permanent medium. The inputs to the Trigger/DAQ system are the digital signals provided by the front-end system. The digitized signals are deserialized and stored in pipeline memories waiting for the trigger decision. If the event is accepted, the DAQ system reads the relevant information in temporary memories, selects the channels identified by the trigger and transfers the information to the data acquisition computer.

The Trigger/DAQ architecture is represented in FIG. 8. It is composed of 3 logic modules, namely the Data Acquisition and Filter (DAQ) module (31), the Trigger module (32) and the Data Concentrator (DCC) module (33) interconnected through two buses (34). The DCC module is connected to the PC (35) by a fast data link (36).

The DAQ module receives digital signals from the front-end system (37). The DAQ module is responsible for evaluating the hit energy and the interaction time for every input channel. For each one, the digital signal is deserialized and stored in a digital pipeline memory at system frequency. The corresponding channel identifier is also stored. In parallel, the data samples are processed to extract the pulse characteristics.

The DAQ module performs the following operations in pipeline mode:
1) Peak search: search for a sample higher than the two neighbors in each channel.
2) Channel sorting and matching: sorting of the detector channel identifiers received from the front-end digital lines and matching between detector channels IDs in the two sides of the detector plate.
3) Pedestal estimation: computation of pedestal and subtraction from the data samples.
4) Normalization: multiplication of the pedestal corrected samples by a normalization coefficient.
5) Energy sum: summation of the pulse amplitude of the four channels corresponding to a front-end chip.
6) Pulse time: the phase between the pulse peak and the clock is computed.

The four-channel energy sum is compared to two programmable thresholds, the event threshold and the Compton threshold. The Compton threshold is used for identify the occurrence of a Compton diffusion and the event threshold is used to identify the absorption of a 511 keV photon. When the energy is above one of the threshold levels, the channel information is transmitted to the subsequent modules. In order to improve throughput, a Filter module eliminates non relevant information. The Trigger module receives information from all the DAQ modules that have detected the occurrence of either a photoelectric absorption or a Compton diffusion. A coincidence occurs when two energy deposits above the event threshold in different crystal planes are detected within a programmable time window.

When a valid coincidence is identified, the Trigger will signal the corresponding DAQ modules that an event is valid and that the associated data must be made available to next processing module. The DCC receives data from all the corresponding DAQs and organizes it into a single package to be sent to the data acquisition PC through a separated data link.

In order to estimate the random coincidence background, random events are also collected. Random events are fictitious events obtained by delaying data associated with one of the two crystal planes in coincidence for a given time interval.

Physically, the Trigger/DAQ system is implemented in a set of boards housed in a 6 U crate with two backplanes. Two types of electronic boards are used, namely the data acquisition boards (DAQ boards) performing deserialization, temporary data storage and algorithmic processing, and the trigger and data concentrator board (Trigger/DCC board) that selects the coincidence events and interfaces to the data acquisition computer through a fast link (~500 Mbyte/s). The trigger and data acquisition logic is implemented in large FPGAs with four million gates.

5.6 Data Acquisition and Control Software

The tasks performed by the data acquisition and control software are the following:

a) Acquisition and Control Tasks:
1. Start/stop/interrupt/resume acquisitions—this includes the user interface in the form of dialog boxes and the low-level routines to control and communicate with the scanner's detection system.
2. Acquisition Protocol Definition Tool—A tool with its own user-interface allowing for the creation and running of acquisition protocols.
3. Emergency stop—low-level routines that allow for the possibility of immediately stopping the movement of the scanner if required, allowing the free manual movement by an operator.
4. Start/stop/define the position and rotation of the scanner during an acquisition—low-level routines that control the position and rotation of the scanner.
5. Display acquisition data in real-time—this includes displaying information of the number of counts detected, elapsed/remaining time, main acquisition parameters, scanner status and preview images of the acquired data.
6. Saving acquired data in different formats—low-level routines for controlling the scanner detection system, reading the data stream and saving to the local disk.
7. Read and save of auxiliary data—routines to read and save parameters used by the data corrections (normalization, deadtime and scatter corrections)

b) Data Correction Tasks:
1. Random correction—this correction estimates the accidental coincidences and subtracts them from the prompt coincidences, using events triggered with the random coincidence trigger.
2. Normalization correction—this correction accounts for efficiency variations in the detection system, due to random variations of the intrinsic crystal efficiency and to the geometry of the system. The measurement of these efficiency parameters is carried out with $^{68}$Ge linear source by detecting the prompt coincidences as the system rotates around the source.
3. Dead time correction—This correction compensates for system deadtime and uses parameters calculated from a dynamic acquisition, performed with a decaying source spanning the full range of count rates.
4. Scatter correction—Scatter correction compensates for Compton scatter which degrades the final contrast of the images and, to some extent, the spatial resolution. The software applies this correction to any acquired exam. Since the detection system gives list-mode information concerning the energy deposited in the detection system by each pair of photons in coincidence, an energy-based scatter correction method is implemented, since these methods are able to account for the scatter component coming from the activity outside the Field of View (FOV), which in the partial-body PET applications is high.

5. Attenuation correction—A simple calculated attenuation correction using a constant attenuation coefficient supplied by the user is implemented.

c) Performance, Diagnostics, Quality Control and Testing Tasks:
1. Communications with the scanner—software to read/write values from/to the front-end registers.
2. Diagnostics and error detection—software that checks all modules for communication errors between the camera and the controlling computer.
3. Normalization procedure—software to perform the acquisition of the normalization data and to calculate the crystal efficiencies.
4. NEMA measurements adapted to partial-body PET—Routines to perform the main performance measurements of the camera, adapted to the partial-body PET case.

5.7 The Image Reconstruction and Analysis Software

The image reconstruction and analysis software allows reconstructing, visualizing and analyzing the data produced during operation. Image reconstruction allows obtaining a representation of a two-dimensional or three-dimensional object from a large number of its projections taken at different positions.

Image Reconstruction Algorithms

A class of analytical algorithms (the algorithms using Filtered Backprojection) based on the inversion of the Radon Transform has been extensively used. In this case, the projections obtained are filtered in the Fourier space before being backprojected to form an image of the object. One of the main drawbacks of the Filtered Backprojection algorithm is the need to perform all image corrections before reconstruction.

Alternatively, the iterative reconstruction algorithms seek to obtain successively more precise estimations of the object's true activity. This procedure allows incorporating in the algorithms a model of the detection process, which may take into account aspects like the object's scattering characteristics, system's geometric constraints or the statistical nature of the data acquisition. Iterative algorithms also allow taking into account some a priori known information about the object, like the absence of negative activity values or the spatial distribution of its anatomical structures (from CT or MRI images).

In practical terms, an iterative image reconstruction algorithm works with five different components: 1) an image of the activity distribution, 2) the system's transfer function to be used, in the form of a matrix A, relating the image matrix f with the matrix containing the expected projection activity values p, 3) a statistical/geometrical model describing the distribution of counts, 4) the objective function to be maximized and 5) the iterative algorithm which is responsible for changing the object's activity in order to maximize the objective function.

The partial-body PET system is prepared to acquire 3D PET information. Therefore, either 3D reconstruction algorithms or 2D reconstruction algorithms using rebbined data may be used. In the first case, all the lines of response (LOR's) are used in the reconstruction process to form a 3D image. In the second case, these LOR's are re-arranged in order to produce a series of 2D like datasets from which the object's image is obtained as a set of axial slices. While 3D reconstruction algorithms can potentially provide better final spatial resolution, 2D algorithms have already been tested and are more rapid. The 2D reconstruction methods use linograms and the ART algorithm while 3D reconstruction is based on the OSEM algorithm.

The image reconstruction algorithms use data acquired in list-mode by the Data Acquisition System. The data acquisition records several characteristics of the photons interacting with the detector (e.g. their energy, place of interaction, time). List-mode data can be binned into sinograms or linograms. The energy and time of the photons is determined accurately before being used for image reconstruction.

The reconstruction procedures starts by using a fast reconstruction method allowing obtaining reconstructed images of the lesion's location within 5 to 10 minutes after data acquisition. We explore the use of this information, obtained either with one or two iterations of the ART algorithm or using the FBP algorithm, to "target" the optimal reconstruction procedure to an area encompassing all the lesions. This area could be of different size, allowing optimizing memory, imaging resolution and reconstruction times.

Image Visualization and Image Analysis Software

The image visualization software is implemented using the IDL System (Research Systems). Routines needing special processing capabilities are developed using C++ and interfaced with IDL. Image visualization and image analysis are integrated in the same software package.

The image visualization software allows to:
1. Accepting binary files and the latest versions of INTERFILE and DICOM.
2. Allowing interactive multiple data selection (at least two datasets).
3. Displaying raw PET data, i.e. data in the form of sinograms or linograms.
4. Scrolling through raw data.
5. Including pull-down menus as interfaces to the reconstruction software operation.
6. Allowing on-line changing of the image reconstruction parameters (image reconstruction algorithm and filters).
7. Viewing of at least two different datasets at the same time.
8. Performing image zooming.
9. Selecting image color scales.
10. Saving and retrieving data from a patient database.
11. Exporting reconstructed data in JPEG and MPEG formats.
12. Printing reconstruction results.
13. Comparing different image modalities on the same screen (e.g. PET and X-Ray).

The image analysis software is included in the same package as the image reconstruction software. This software allows:
1. Selecting Regions of Interest (ROI) on the image (either geometrical shapes or line profiles). These ROI should be either 2D or 3D (i.e. encompassing several slices in the reconstructed image).
2. Measuring the reconstructed image spatial 3D resolution.
3. Extracting statistical information from image and ROIs (e.g. maximum count number, mean and variance).
4. Evaluating image uniformity.
5. Performing arithmetic operations with images.
6. Image smoothing.
7. Calculating recovery coefficients for hot lesions (for evaluation studies using phantoms)
8. Calculating lesion dimensions using ROI or other techniques like ROI segmentation.
9. Evaluating image quantification.
10. Calculating SUV values.

5.8 Application to Positron Emission Mammography

The present innovation allows Positron Emission Mammography (PEM), that is the application of PET technology to the detection of breast cancer. This application is offered for illustration and not by way of limitation.

Generic Clinical Requirements

The PEM system should implement the following generic clinical requirements:
1) The PEM system should allow to exam both the breast and the lymph node area (axilla).
2) The breast exam should produce 3D tomographic images capable to guide an automatic stereotatic biopsy system or chirurgical intervention.
3) The axilla exam should produce images allowing to diagnose the presence of cancer cells irrespective of its precise location (yes/no diagnostic).
4) The breast image spatial resolution should be smaller than 2 mm, in the three space coordinates. This parameter determines the precision in localizing lesions with the technique.
5) For the axilla spatial resolution should be in the range 2-3 mm.
6) The detector technical specifications should be designed so that the camera is sensitive to small breast and axilla tumors (1-2 mm), as long as the FDG uptake matches the detector sensitivity and overcomes the background noise.
7) The PEM detector should be combined with an examination table allowing the exams of the different areas to be performed with the patient in prone position.
8) Access of the PEM detector to the breast is provided through holes in the examination table.
9) For breast exams, fixation parts should be used to keep the breast motionless.
10) The PEM system should be designed to be compatible with stereotatic biopsy system or an X-ray mammography.

In general terms, the above specifications are fulfilled by the partial-body PET concept since:
a) Two detecting plates with dimensions that match the dimensions of the breast and axilla region may form the partial-body PET detector.
b) The two plates can rotate around the PET axis allowing taking breast data in several orientations as needed for tomographic image reconstruction.

Performance Requirements

Detection sensitivity (fraction of accepted two-photon events) should be as high as possible in order to reduce the injected dose and the examination time. A value of 40 cps/kBq in the center of the Field Of View (FOV) when the PEM plates are 10 cm apart is acceptable.

The PEM detector will be subject to a large radiation field due to the activity deposited in the body. This radiation is responsible for background events (random coincidences) that affect the image quality. The PEM system should reduce this background to a level below 20% of the true rate.

Present estimates indicate that the rate of true coincidences is between 40 and 250 kHz for a total activity of 10 mCi, depending on the PEM plate separation and on the breast uptake fraction. The same estimations indicate that the total photon rate in the detector (single events) is between 2 and 3 MHz, depending on the detector shielding. This performance is well within the capabilities of the partial-body PET system.

The PEM detector is required to be sensitive to small tumors (2 mm) with a statistical significance above 3 and a data acquisition time of the order of 1 nm. Assuming a smooth background radiation from the breast tissue, the significance reflects the probability that a statistical fluctuation emulates a tumor signal. For a significance of 3 this probability if of the order of 1%, and it is negligible for significance equal to 5.

Geometrical Configuration

The description that follows is based on the drawings of a non-restrictive character that are attached hereto, in which:

FIG. 1 shows a schematic representation of the PEM system in position for breast exam. The examination table and the PEM system are independent units. A motorized system allows the adjustment of the table height.

The PEM system vertical position is adjusted relative to the table to allow the best fit between the detector and the examined anatomical region.

Two detecting plates form the PEM detector itself. The separation distance between the plates can be adjusted under operator control. For safety reasons, a minimum separation between the plates is built-in. The maximum separation is 60 cm.

The two plates are able to rotate around the PEM axis, under computer control, allowing taking breast data in several orientations as needed for the reconstruction of tomographic images.

The active area of the PEM plates (crystal area) is of the order of 17×15 cm, where the longest dimension is measured along the axis perpendicular to the examination table.

Access to the breast is provided through a hole in the examination table, allowing one breast to hang when the patient is in prone position. The vertical distance between the PEM plates and the table is adjustable under operator control to allow the best match between the breast and the PEM device.

To exam the axilla region (or the breast in the front-back configuration) the PEM detector is rotated 90° and an image is produced with one plate below the table and the other over the patient shoulder (or back). In order to allow the exam of the second axilla the detector is moved to the complementary position.

The examination table has the right geometry to stop the activity from outside the field of view and should include as much shielding material as possible.

For breast exams, fixation parts allow to keep the breast motionless. The fixation parts are independent of the detecting plates therefore not disturbing the rotation motion of the PEM detector plates.

The fixation parts are removable so that different shapes may be used for a best possible match with the breast anatomy. Alternatively fixation parts with adjustable forms could be used.

PEM Operational Specifications

After FDG injection and the waiting period for FDG diffusion, the examination procedure is composed of three parts:
1) Patient positioning and detector setting-up
2) Data acquisition
3) Image reconstruction and analysis The sequence of operations involved in the breast exam is the following:
1) The table is prepared for breast exam (single breast hole created with movable parts). The patient is placed on the table in prone position.
2) The operator adjusts the height of the PEM plates in order to bring the PEM plates close to the patient chest.
3) The breast fixation parts are installed and adjusted so that the breast is kept motionless.
4) The operator adjusts the separation between the PEM plates. A minimal separation between the plates is built-in.
5) In the computer control screen the operator sets the exam parameters, in particular the angular orientations of the PEM plates to be used and the data acquisition time.

In the configuration described previously, the breast region close to the chest is badly covered. In order to get supplementary information in this difficult area, an exam can be made where one PEM plate is paced against the breast and the second plate is placed against the patient back. In this configuration, an image of the body region between the two plates can be obtained.

To perform a breast exam in the front-back configuration, the patient is kept in prone position and the PEM detector is rotated by 90°. The position of the PEM plates is then adjusted. One plate is placed below the table, facing the breast, and the second is placed close to the patient back.

Opening the plate separation and rotating the plates (by angles±15°) is possible to obtain data at different angular orientations.

The axilla exam is similar to the complementary breast exam. The patient is kept in supine position with the arm extended leaving the axilla open and free to be examined. The PEM detector is rotated by 90°. The position of the PEM plates is then adjusted. One plate is placed below the table, facing the shoulder, and the second is placed close to the patient torax. Opening the plate separation and rotating the plates is possible to obtain data at different angular orientations.

6. VALIDATION OF THE INVENTION

6.1 Experimental Validation of the Detector Concept

A setup for characterizing radiation sensors and measuring the properties of the detector modules was implemented. This setup consists of a LYSO:Ce matrix composed of 32 individual 2×2×20 mm$^3$ pixels optically coupled on both sides to Hamamatsu S8550 APD matrices, read by discrete front-end electronics based on Cremat CR-101D preamplifiers and a VME-based data acquisition system with multi-channel peak-sensing ADCs.

FIG. 9 shows the energy spectrum (in ADC channel units) obtained with the LYSO crystal matrix and S8550 APD readout. The result was obtained with single APD readout (light collection only on one side of the LYSO:Ce matrix, the other side having a 500 mm thick Teflon reflector). The temperature was stabilized at 20° C. The curves show the spectrum of background photons as well as the characteristic photoelectric peaks of 511 keV photons from a $^{22}$Na source and of 662 keV from a $^{137}$Cs source. The measured energy resolution of the 511 keV peak is 13%.

The temperature dependence of the radiation sensors was evaluated from 11° C. to 43° C.

FIG. 10 shows the temperature dependence of the photopeak positions, for an APD bias voltage of 370 V. It shows that the amplitude of the detector signals decreases by 40% when the temperature increases from 15° C. to 30° C. Between 18° C. and 32° C. the noise increases by a factor 2. At 20° C. the noise FWHM is of the order of 5 keV, showing that the signal to noise ratio at the 511 keV photopeak is of the order of 100. These results demonstrate the importance of cooling and thermal stability, as the noise is considerably smaller and the gain larger at lower temperatures.

The depth-of-interaction in LYSO: Ce crystals was evaluated by measuring the light at both ends of 2×2×20 mm$^3$ crystals. Results from the first set of measurements have shown a linear correlation between the depth-of-interaction and the asymmetry of light collected at both ends of the crystal, for an optimal combination of crystal roughness and optical wrapping.

FIG. 11 shows the DoI estimator as a function of the photon beam coordinate. The error bar represents the FWHM of the asymmetry distribution at each coordinate. The horizontal projection of the error bars on the fitted line defines the FWHM interval of the DoI measurement (around 1 mm).

These experimental results provide proof of the following principles which are at the basis of the present innovation:

- The proposed detector module detects photons with an energy resolution of 13% at 511 keV. This value confirms the expected detector module performance in terms of crystal light yield, light collection efficiency and APD gain.
- Based on these measurements the expected charge at the APD output for a 511 keV photon interacting in the crystal center (assuming equal light sharing on the two crystal end faces) is on average 15 fC.
- The measured energy resolution is adequate for the implementation of the Compton identification algorithms, as indicated by the simulation results presented in section 6.2.
- The detector should operate at the stabilized temperature of 20° C. in order to achieve the needed levels of signal amplitude and noise.
- The detector channels have a FWHM noise level of 5 keV, obtained with discrete front-end amplifiers. These results show that the desired overall low noise level (APD and electronics) can be achieved provided the integrated front-end chip under development has similar noise performance.
- For the measured signal to noise ratio, the expected time resolution of a 511 keV photon interacting in the crystal center (worst case) is 390 ps r.m.s, confirming the design value.
- The LYSO light collecting system provides an asymmetry between the light collected at the extremities that varies linearly with the photon impact point. This fact is used to extract the depth of interaction with a resolution of the order of 1 mm.

6.2 Estimation of PEM Performance

An evaluation of the PEM system performance was obtained using Monte Carlo simulation techniques. The simulation is performed on an event-by-event basis. For each event the elementary physics processes that govern the interaction of photons with matter are simulated according to probabilistic distributions. The process of signal formation in the crystal and associated electronics is simulated as well.

The simulation study used the GEANT4 package for the whole ensemble of Monte Carlo simulations. A modular application was developed, which includes the simulation of radioactive decay and photon tracking in phantoms (PhantomFactory module), detector response (PEMsim module) and the processes of signal formation in front-end electronics and DAQ system (DIGITsim module).

In the PEMsim module the number and dimension of crystals, dead spaces due to crystal wrapping, presence of front-end electronics and optical parameters are defined. Reflector coatings and optical glues are specified in terms of their optical properties. Full characterization of crystal scintillator includes the emission spectra, nominal light yield and associated time decay constant. As input PEMsim uses data from PhantomFactory module.

The front-end electronics, the trigger and the data acquisition system are simulated in the DIGITsim. This module converts the information from each PEMsim hit into a pulse shape, adds electronic noise and performs the signal A/D conversion. From the digitized dataframe the reconstruction of energy and time are also performed. Reconstructed simulated events are then interfaced with image reconstruction software.

To evaluate the detection sensitivity, a point source emitting back-to-back 511 keV photons in air was positioned along one of the detector axis in the central plane of the FoV. The sensitivity profile is shown in FIG. 12 where different separation distances between the detector heads were considered. The peak sensitivity values for the three separation distances were found to be 9.3% (5 cm), 5.9% (10 cm) and 4.0% (15 cm).

Due to in-detector Compton scatter, 70% of PEM coincidences have at least a Compton diffusion in the detector. In this case, two crystals will share the deposited energy. These events are accepted in order to achieve high detection sensitivity. Acceptance of Compton events can, however, degrade the spatial resolution, due to ambiguities in the identification of the crystal where the first interaction took place. Using Monte Carlo data containing two-hit events, several algorithms for first crystal identification were evaluated. The reconstruction algorithm based on Compton kinematics has an efficiency of 89.4%. This high-performance is possible due to the good DoI resolution.

An anthropomorphic phantom was implemented in the simulation code which allows for an accurate modelling of the background events from non-breast uptake. Each volume corresponding to an organ or anatomical structure in the phantom was filled with a FDG radiotracer concentration, according to tabulated standardized uptake values (SUVs) measured one hour after the injection of 370 MBq. The results have shown a true coincidence count-rate up to 250 kHz, depending on detector heads distance and breast FDG uptake. A maximum single photon rate of 1.5 MHz per detector head was obtained as well as a rate of random coincidences of 20 kHz. No radiation shields were included.

Seven point sources placed in the scanner field-of-view (FoV) in a cross formation (cross-phantom) were fully simulated.

FIG. 13 shows the transaxial central plane of this phantom obtained by the reconstruction the simulated data. Activity corresponding to the point sources is confined to 2 reconstruction pixels representing a spatial resolution of approximately 1 mm.

The following table shows the estimation of data acquisition time needed to have a given statistical significance (as defined in section) in the detection of 1 mm tumors. The results are shown as a function of the PEM detector sensitivity. The calculation assumes an FDG injected dose of 10 mCi, an uptake in the breast of 0.5% (50 µCi) and a ratio of FDG absorption lesion/tissue of 3.

| Sensitivity | 100 cps/kBq | 50 cps/kBq | 20 cps/kBq |
|---|---|---|---|
| Significance = 3 | 28 s | 55 s | 2 mn 18 s |
| Significance = 5 | 1 mn 16 s | 2 mn 33 s | 6 mn 22 s |

The invention clamed is:

1. A Positron Emission Tomography (PET) system dedicated to close examination, at a few millimeters from the skin, of human body parts including the breast, axilla, head, neck, liver, heart, lungs, prostate region and other body extremities or, to the detection and follow-up of different types of cancers in of the human body, that integrates in two movable, light-weight and compact PET detector heads the large number of individual detection channels, more than 12000 channels, based on LYSO (Cerium Doped Lutetium Yttrium Orthosilicate) crystals and avalanche photo-diodes (APD) arrays, with a small number of interconnections to a trigger and data acquisition system, necessary to allow high-sensitivity and image resolution of 1 mm in the full field-of-view comprised between two detection plates of LYSO crystals, and that is characterized by:
   a. two detector heads housing more than 6000 LYSO crystals each with dimensions of the order of 2×2×20 mm$^3$, two avalanche photodiodes per crystal pixel, electronic front-end readout system for each APD detection channel, and ancillary systems, the detector heads having a density larger than 0.5 detection channels per cm$^3$;
   b. means for measuring of the coordinates of the photon interaction point in the detector with a precision of the order of 1 mm in the three space directions, by using fine-grained crystal granularity and a means for measuring a depth of interaction based on the sharing of scintillating light at the two ends of the crystal pixels;
   c. a means for detecting and measuring individual hits of Compton events in the detector and in consequence to use in image reconstruction the events where at least one of the two PET photons has Compton diffusion in the detector, without significant degradation of the image resolution;
   d. motorized mechanical means to allow the movement of the detector heads under manual or computer control, including the rotation around two independent axis and the translation along three perpendicular axis, plus the relative positioning of the two detector heads, making it possible to place the detector heads in plural orientations, as more appropriate for the organ under examination, and in contact with the patient skin for maximum sensitivity, and to collect data in several orientations as needed for tomographic image reconstruction with sensitivity as high as 0.10 cps/Bq;
   e. a data-driven and synchronous architecture of the electronic front-end readout system that provides to each individual APD detection channel, low-noise amplification, pulse sampling at clock frequency, analog pipeline storage, event detection, and that provides input channel selection and multiplexing to the circuit output of the two-highest energy inputs, operating in pipeline mode with fixed latency at frequencies up to 100 MHz, implemented in an application-specific integrated electronics circuit handling 192 input channels;
   f. a means for on-line measurement by the trigger system of the photons detection time, without introducing dead time in the data acquisition process, based on the analog-to-digital conversion of detector pulse samples and on a digital algorithm to compute the photon event time, as required by a two-photon coincidence trigger with time resolution of the order of one nanosecond; and
   g. an architecture of the trigger and data acquisition system, based on the combination of a pipelined synchronous section followed by a dual-bus asynchronous readout system, capable to operate at a rate of one million coincidence events per second, for a background photon interaction rate of 10 million photons per second as expected in partial-body PET system operation under the large background of radiation from the whole-body and without shielding in the detector heads.

2. The Positron Emission Tomography (PET) system according to claim 1, characterized in that each of the detector heads is composed of a plurality of detector modules, which consist of units providing a plurality of high density scintillating photon detector crystals LYSO (Cerium doped Lutetium Yttrium Orthosilicate) with a density of 7.4 g.cm$^{-3}$, a light yield of about 27 photons/keV, an emission spectrum peaking at 430 nm, a signal with a time constant of 40 ns and with dimensions 20×2×2 mm, optically isolated in a 4×8 arrangement coupled to APD (Avalanche Photo-Diode) arrays at both ends, the crystals and the APD arrays being housed and sealed in a plastic mechanical assembly and the transverse dimensions of the crystals being determined by the desired spatial resolution, whereas the longitudinal dimension is dictated by the required detector sensitivity.

3. The Positron Emission Tomography (PET) system according to claim 2, characterized in that the APD arrays of 4×8 diodes convert the crystal light into an electrical signal, the pixel effective size being compatible with the planned crystal transverse size, the APD pixel effective size is 1.6×1.6 mm$^2$ and the quantum efficiency at the LYSO emission peak is about 75%, the APD gain is around 50, the dark current is of the order of 2-4 nA, the capacitance is 9 pF and the said gain has a temperature gradient of −2.4%/° C., which implies that the system has to operate under stabilized thermal conditions.

4. The Positron Emission Tomography (PET) system according to claim 2, characterized in that the optical parameters of the crystal light collection into the APD pixels are designed and experimentally validated to achieve the gradient of light sharing between the top and bottom APDs necessary for a measurement of Depth-of-Interaction with a resolution of the order of two millimeters, the said parameters being that the LYSO crystal lateral surfaces are slightly polished with the roughness parameter Ra comprised between 1500 and 2000 Angstroms, the top and bottom surfaces are polished with Ra less than 100 Angstroms, the crystal pixel wrapping is made of BaSO$_4$ (barium sulphate) with 250 μm thickness, which wrapping provides the crystal support and enclosure, the crystal top and bottom surfaces are optically coupled to the APD array epoxy with a layer of thickness 20 μm of optical grease with refraction index 1.6, matching the epoxy refraction index.

5. The Positron Emission Tomography (PET) system according to claim 1, characterized in that the motorized mechanical means permit:
a. vertical movement, allowing the adjustment of the plates height;
b. horizontal movements in two directions, allowing the adjustment of the plates position;
c. relative positioning of the two detector heads, allowing to adjust the plate separation;
d. rotation of the PET plates around the PET axis, allowing optimal positioning of the detector heads and optimizing tomographic image reconstruction; and
e. rotation of the PET system around a second axis, which combined with first rotation axis allowing examinations with the detector heads oriented in plural directions.

6. The Positron Emission Tomography (PET) system according to claim 1, characterized in that the electronic front-end readout system, based in an application-specific integrated circuit (ASIC) handling 192 input channels, has a specific data-driven synchronous architecture operating in pipeline mode at frequencies up to 100 MHz as required for the operation of the described PET system, the said architecture providing for each input APD pulse the corresponding output data samples synchronously with the system clock, the output data being generated only in case the data corresponds to a photon with energy above a programmable threshold (data-driven auto-trigger), and with a fixed time interval (latency) between the input signal and the output data as required by the coincidence trigger system.

7. The Positron Emission Tomography (PET) system according to claim 6, characterized in that the electronic front-end readout system has for each APD detection channel a low-noise amplifier characterized by a maximum input charge of 30 femto-Coulomb, an input equivalent noise charge (ENC) below 1000 electrons, a power dissipation below 3 milli-Watt per channel, a radiation tolerance up to 5 kilo rad total dose, an output signal shaping with peaking time of 30 nanoseconds and a gain of 30 milliVolt/femtoCoulomb.

8. The Positron Emission Tomography (PET) system according to claim 6, characterized in that the electronic front-end readout system provides signal amplitude sampling at the output of the amplifiers and at every clock period, stores the sampled charges in capacitor arrays which work as a circular pipeline analog memories, and in parallel processes the analog signals by comparators followed by digital logic to determine the channels above threshold.

9. The Positron Emission Tomography (PET) system according to claim 6, characterized in that the electronic front-end readout system, for the input signals above threshold, reads from the analog memories ten data samples and multiplexes the data to one of two available output channels at system clock frequency, together with the corresponding input channel identification coded as a ten bit data stream synchronous to the analog data samples, thus providing a data compression factor of 192 to 2, as required by the compact and movable PET detector heads.

10. The Positron Emission Tomography (PET) system according to claim 9, characterized in that the electronic front-end readout system is composed of a certain number of front-end boards (FEB) per detector head, providing a direct interface to the top and bottom sides of detector modules, and a service board for clock distribution, power supply distribution, bias voltage regulation and temperature monitoring, each FEB corresponding to a certain number of crystal modules, and each FEB including:
a certain number of front-end integrated circuits (ASIC) with 192 channels;
a free running analog-to-digital (ADC) sampling converter at frequency up to 100 MHz for each of the ASIC output channels, followed by a parallel-to-serial converter for each group of two ASICs;
plural fast data links, each working at frequencies up to 680 MHz, using electrical flat cables with 10 differential pairs each;
plural flat cable connectors for control and clock lines, for reading the temperature sensors and for distribution of low voltage;
plural flat cable connectors for APD bias voltage distribution, one independent voltage per 16 APD pixels.

11. The Positron Emission Tomography (PET) system according to claim 1, characterized in that the trigger and data acquisition system receives from the front-end system digitized data streams synchronously to the electron-positron annihilation events, estimates in a time shorter than 100 ns the energy and time of the detected photons in the two opposite detector heads, selects those photons with energy compatible with 511 keV or finds groups of hits that correspond to photons with Compton diffusion in the detector heads, compares the times of plural combinations, and reads the data of the relevant channels into the computer memory and disk when a coincidence is found.

12. The Positron Emission Tomography (PET) system according to claim 11, characterized in that trigger and data acquisition system comprises pipeline processing structures used to compute the pulse amplitude and time, combined with pipeline memories for data storage during the trigger processing time, which combination allows for on-line coincidence triggering without introducing data acquisition dead-time.

13. The Positron Emission Tomography (PET) system according to claim 11, characterized in that the trigger and data acquisition system is composed of three logic modules, the Data Acquisition and Filter (DAQ) modules, one per front-end data link, DAQ modules which process in parallel the front-end data, the Trigger module and the Data Concentrator (DCC) module, all modules interconnected through two data buses, a trigger bus and a data acquisition bus, and the DCC module is connected to the PC by a fast data link.

14. The Positron Emission Tomography (PET) system according to claim 13, characterized in that the DAQ module is responsible for computing the photon energy and the interaction time for every input channel, performing the following operations in pipeline mode:
   a. Peak search: search in the input data stream for a data sample higher than the previous and the following data samples in each channel;
   b. Channel sorting and matching: sorting of the detector channel identifiers received from the front-end digital lines and matching between detector channels identifiers in the two sides of the detector plate;
   c. Baseline estimation: computation of signal baseline as the average of two pre-samples (samples before the pulse rising-edge) and subtraction from the data samples;
   d. Normalization: multiplication of the baseline corrected samples by a programmable normalization coefficient;
   e. Photon Energy sum: summation of the pulse peak amplitude of the four output channels of two matching front-end ASICs; and
   f. Photon Interaction time: computation of the pulse time, given by the clock number at pulse reception (coarse grain time) associated to the phase between the pulse peak and the clock (fine grain time), the fine grain time being computed has the ratio of the peak sample amplitude to the previous sample amplitude, multiplied by a normalization coefficient, of the highest pulse in the four channels involved in the energy computation.

15. The Positron Emission Tomography (PET) system according to claim 14, characterized in that the four-channel energy sum is compared to two programmable thresholds, the event threshold and the Compton threshold, the Compton threshold being used to identify the occurrence of a Compton diffusion in the detector and the event threshold being used to identify the absorption of a 511 keV photon, and when the energy is above one of the threshold levels the channel information is transmitted, via the Trigger bus, to the Trigger module which receives information from all the DAQ modules that have detected the occurrence of either a photoelectric absorption or a Compton diffusion.

16. The Positron Emission Tomography (PET) system according to claim 13, characterized in that a Trigger module detects a coincidence trigger when energy deposits above the event threshold in the two crystal planes are detected within a programmable time window, in which case the Trigger module sends a signal the corresponding DAQ modules that the event is valid, and the DAQ modules send the associated data, via the data acquisition bus, to the DCC module, which receives data from all the corresponding DAQs and organizes it into a single package to be sent to the data acquisition PC through a separated data link.

17. The Positron Emission Tomography (PET) system according to claim 13, characterized in that the trigger and data acquisition system is implemented in five boards of two different types, four data acquisition boards implementing the DAQ modules, each data acquisition board corresponding to 8 DAQ modules, and one central trigger and data concentrator board, implementing the Trigger and DCC modules, using Field Programmable Gate Arrays (FPGAs) with four million gates to implement the trigger and data acquisition logic and memories, which boards are housed in a crate of 6 U format with two backplane buses with Peripheral Computer Interface (PCI) connectors implementing the trigger and the data acquisition transmission buses.

18. A Positron Emission Tomography (PET) system dedicated to close examination of human body parts, comprising:
   (a) two detector heads, each comprising (1) a plurality detection modules, each module having a plurality of LYSO crystals and a plurality of avalanche photodiodes, each LYSO crystal being combined at opposite ends with an avalanche photodiode (APD) to define a crystal pixel coupled to an APD detection channel, (2) an electronic front-end readout system for each APD detection channel, and (3) ancillary systems,
   wherein each detector head has a density larger than 0.5 detection channels per $cm^3$,
   wherein the measurement of coordinates of a photon interaction point in the detector has a precision of the order of at least 1 mm in three spacial directions, by using fine-grained crystal granularity and by measuring a depth of interaction based on the sharing of scintillating light at the two ends of the crystal pixels,
   wherein the detector head is operative to detect and measure individual hits of Compton events and in consequence to use in image reconstruction events where at least one of two PET photons has Compton diffusion in a detector module, without significant degradation of image resolution; and
   wherein each electronic front-end readout system has a data-driven and synchronous architecture that provides to each individual APD detection channel, low-noise amplification, pulse sampling at clock frequency, analog pipeline storage and event detection, and that provides input channel selection and multiplexing to the circuit output of the two-highest energy inputs, operating in pipeline mode with fixed latency at frequencies up to 100 MHz, implemented in an application-specific integrated electronics circuit;
   (b) motorized mechanical means to provide movement of said detector heads under manual or computer control, by rotation around two independent axis and translation along three perpendicular axis, plus the relative positioning of the detector heads,
   wherein said detector heads may be placed in plural orientations, as appropriate for a target under examination and in contact with a patient's skin for maximum sensitivity, and for collecting data in several orientations as needed for tomographic image reconstruction with sensitivity as high as 0.10 cps/Bq; and
   (c) a trigger and data acquisition system, having an architecture comprising a combination of a pipelined synchronous section followed by a dual-bus asynchronous readout system, operate at a rate of at least one million coincidence events per second, for a background photon interaction rate of at least 10 million photons per second as expected in partial-body PET system operation under the large background of radiation from the whole-body and without shielding in the detector heads,
   wherein the trigger and data acquisition system performs on-line measurement of the photons detection time, without introducing dead time in the data acquisition process, based on the analog-to-digital conversion of detector pulse samples and on a digital algorithm to compute the photon event time, as required by a two-photon coincidence trigger with time resolution of the order of at least one nanosecond.

* * * * *